United States Patent
Crooks et al.

(10) Patent No.: US 9,550,753 B2
(45) Date of Patent: Jan. 24, 2017

(54) MONO QUATERNARY AMMONIUM SALTS AND METHODS FOR MODULATING NEURONAL NICOTINIC ACETYLCHOLINE RECEPTORS

(71) Applicant: University of Kentucky Research Foundation, Lexington, KY (US)

(72) Inventors: Peter Crooks, Little Rock, AR (US); Linda P. Dwoskin, Lexington, KY (US); Guangrong Zheng, Lexington, KY (US); Sangeetha Sumithran, Lexington, KY (US); Zhenfa Zhang, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 14/470,715

(22) Filed: Aug. 27, 2014

(65) Prior Publication Data
US 2014/0371266 A1    Dec. 18, 2014

Related U.S. Application Data

(62) Division of application No. 12/304,955, filed as application No. PCT/US2007/014192 on Jun. 15, 2007, now Pat. No. 8,846,937.

(60) Provisional application No. 60/814,423, filed on Jun. 16, 2006.

(51) Int. Cl.
| | | |
|---|---|---|
| C07D 211/92 | (2006.01) |
| C07D 401/14 | (2006.01) |
| C07C 17/16 | (2006.01) |
| C07D 213/20 | (2006.01) |
| C07D 213/30 | (2006.01) |
| C07D 215/10 | (2006.01) |
| C07D 217/10 | (2006.01) |
| C07D 401/06 | (2006.01) |

(52) U.S. Cl.
CPC ............. *C07D 401/14* (2013.01); *C07C 17/16* (2013.01); *C07D 213/20* (2013.01); *C07D 213/30* (2013.01); *C07D 215/10* (2013.01); *C07D 217/10* (2013.01); *C07D 401/06* (2013.01)

(58) Field of Classification Search
None
See application file for complete search history.

(56) References Cited

U.S. PATENT DOCUMENTS

| 7,018,797 B2 | 3/2006 | Reitz et al. |
| 2005/0215571 A1 | 9/2005 | Romano |
| 2005/0282823 A1 | 12/2005 | Breining et al. |

OTHER PUBLICATIONS

Ayers, J. Bioorg. Med. Chem. Lett. 2002 vol. 12 pp. 3067-3071.*
CAPLUS 1938:42453.*
CAPLUS 1958:32032.*
CAPLUS 1958:2183.*
CAPLUS 1952:8600.*
CAPLUS 1946:20771.*
CAPLUS 2004:1057504.*
Bahner, C et al J Amer Chem Soc 1951 vol. 73 pp. 3499-3535.*
International Search Report dated Nov. 23, 2007 (One (1) page).
Silverman, R., "The Organic Chemistry of Drug Design and Drug Action", 2004, Elsevier, pp. 29-32.
HCAPLUS 1988:565166.
HCAPLUS 1993:249523.
Ayers, J. et al., Bioorg. Med. Chem. Lett. (2002), vol. 12(21), pp. 3067-3071.
Bergmeier, S. et al., Bioorg Med. Chem. Lett. (1999), vol. 9, pp. 2263-2266.
Allen, D. et al., J. Pharmacol Exp. Thera, 2003, vol. 304, pp. 1268-1274.
Olbrich, C. et al., J. Nanopart. Res., 2002, vol. 4, pp. 121-129.
Grinevich, V. et al., J. Pharmacol. Exper. Thera, 2003, vol. 306, pp. 1011-1020.
Dwoskin, L. et al., Bioorganic & Medicinal Chemistry Letter 2004, vol. 14(8), pp. 1863-1867.

* cited by examiner

*Primary Examiner* — Heidi Reese
(74) *Attorney, Agent, or Firm* — Crowell & Moring LLP

(57) ABSTRACT

Provided are monoquaternary ammonium compounds which are modulators of nicotinic acetylcholine receptors. Also provided are methods of using the compounds for modulating the function of a nicotinic acetylcholine receptor, and for the prevention and/or treatment of central nervous system disorders, substance use and/or abuse, and gastrointestinal tract disorders.

10 Claims, No Drawings

MONO QUATERNARY AMMONIUM SALTS AND METHODS FOR MODULATING NEURONAL NICOTINIC ACETYLCHOLINE RECEPTORS

CROSS REFERENCE TO RELATED APPLICATION

This application is a divisional of U.S. application Ser. No. 12/304,955, which is a National Stage of PCT/US2007/014192, filed on Jun. 15, 2007, which claims benefit of U.S. Provisional Application No. 60/814,423, filed Jun. 16, 2006, which are expressly incorporated herein by reference herein.

IDENTIFICATION OF FEDERAL FUNDING

The present invention was supported by Grant NIH U19DA017548 from the National Institutes of Health, and therefore the government may have rights in the invention.

FIELD OF THE INVENTION

The invention relates to monoquaternary ammonium salts and their use in modulating nicotinic acetylcholine receptors.

BACKGROUND OF THE INVENTION

S(−)-nicotine (NIC) activates presynaptic and postsynaptic neuronal nicotinic receptors that evoke the release of neurotransmitters from presynaptic terminals and that modulate the depolarization state of the postsynaptic neuronal membrane, respectively. Thus, nicotine produces its effect by binding to a family of ligand-gated ion channels, stimulated by acetylcholine (ACh) or nicotine which causes the ion channel to open and cations to flux with a resulting rapid (millisecond) depolarization of the target cell.

Neuronal nicotinic receptors are composed of two types of subunits, α and β, and assemble as heteromeric receptors with the general stoichiometry of 2α and 3β or as homomeric receptors with 5α subunits. Nine subtypes of the α subunit (α2 to α10) and three subtypes of the β unit (β2 to β4) are found in the central nervous system. The most common nicotinic receptor subtype in the brain is composed of two α4 and three β2 subunits, i.e., α4β2. These subunits display different, but overlapping, patterns of expression in the brain. Examples of heteromeric receptor subtypes include α4β2, α3β2, α3β4, α6β2, α4α5β2, α6α5β2, α4α6β2, α4β2β4, α3β2β4, and others. The predominant homomeric subtype includes α7, but other combinations have also been proposed.

For the most part, the actual subunit compositions and stoichiometries of nicotinic receptors in the brain remain to be elucidated. Thus, neuronal nicotinic receptor subtype diversity originates from differences in the amino acid sequence at the subunit level and from the multiple combinations of assemblies of subunits into functional receptor proteins, which affords a wide diversity of pharmacological specificity.

In spite of the extensive diversity in neuronal nicotinic receptor messenger RNA expression, only a limited number of tools are available to study the pharmacology of native receptors. Radioligands are used in many studies. [$^3$H]NIC appears to label the same sites in the brain as [$^3$H]ACh. It has been estimated that over 90% of [$^3$H]NIC binding in the brain is due to association with the heteromeric receptor that is composed of α4 and β2 subunits. Also abundant in the central nervous system are the homomeric receptors labeled by [$^3$H]methyllycaconitine (MLA), which has high affinity for the α7 nicotinic receptor subtype. Nicotinic receptor subtypes can be studied using functional assays, such as NIC-evoked neurotransmitter release (e.g., [$^3$H]dopamine (DA) release, [$^3$H]norepinephrine (NE) release, [$^3$H]serotonin (5-HT) release, [$^3$H]gamma-aminobutyric acid (GABA) release and [$^3$H]glutamate release) from superfused rat brain slices. Nicotinic receptors are located in the cell body and terminal areas of these neurotransmitter systems. NIC facilitates neurotransmitter release from nerve terminals.

The structural and functional diversity of central nervous system nicotinic receptors has stimulated a great deal of interest in developing novel, subtype-selective agonists and/or antagonists. Some of these agonists are currently being evaluated in clinical trials for cognitive enhancement and neuroprotective effects, potentially beneficial for disease states such as Alzheimer's and Parkinson's disease.

SUMMARY OF THE INVENTION

In one embodiment, compounds corresponding to the following structure are provided.

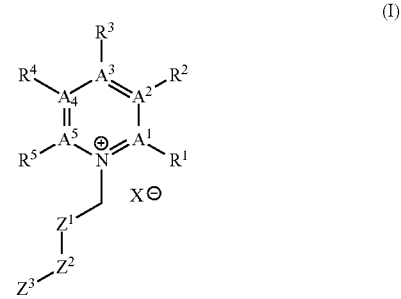

(I)

$A^1$, $A^2$, $A^3$, $A^4$, and $A^5$ are independently selected from nitrogen or carbon, provided that when nitrogen is present, the nitrogen does not have an R substituent attached.

$R^1$, $R^2$, $R^3$, $R^4$, and $R^5$ are each independently selected from the group consisting of hydrogen, alkyl, substituted alkyl, cycloalkyl, substituted cycloalkyl, alkenyl, substituted alkenyl, alkynyl, substituted alkynyl, aryl, substituted aryl, heterocycle, substituted heterocycle, halo, cyano, and nitro, or $R^1$ and $R^2$ or $R^2$ and $R^3$ together with the carbons to which they are attached independently form a three to eight-member cycloalkane, substituted cycloalkane, cycloalkene, substituted cycloalkene, aryl, substituted aryl, heterocycle with one to three hetero atoms in the ring, or substituted heterocycle with one to three hetero atoms in the ring.

$Z^1$ is absent or is selected from the group consisting of alkyl, substituted alkyl, cycloalkyl, substituted cycloalkyl, alkenyl, substituted alkenyl, alkynyl, substituted alkynyl, phenylene, substituted phenylene, alkoxy, and substituted alkoxy.

$Z^2$ is selected from the group consisting of alkyl, substituted alkyl, cycloalkyl, substituted cycloalkyl, alkenyl, substituted alkenyl, alkynyl, substituted alkynyl, arylene, substituted arylene, heterocycle, substituted heterocycle, alkoxy, and substituted alkoxy.

$Z^3$ is selected from is selected from hydrogen, alkyl, substituted alkyl, cycloalkyl, substituted cycloalkyl, alkenyl, substituted alkenyl, alkynyl, substituted alkynyl, aryl, substituted aryl, heterocycle, and substituted heterocycle.

$X^-$ is an inorganic or organic anion.

In another embodiment, a composition is provided comprising a pharmaceutically acceptable carrier and a compound as described above.

In another embodiment, a method is provided for selectively modulating the function of a nicotinic acetylcholine receptor comprising administering a therapeutically effective amount of a compound as described above to a mammalian subject in need thereof.

In another embodiment, a method is provided for preventing and/or treating a central nervous system associated disorder comprising administering a therapeutically effective amount of a compound as described above to a mammalian subject in need thereof.

In another embodiment, a method is provided for preventing and/or treating substance use and/or abuse comprising administering a therapeutically effective amount of a compound as described above to a mammalian subject in need thereof.

In another embodiment, a method is provided for preventing and/or treating gastrointestinal tract disorders comprising administering a therapeutically effective amount of a compound as described above to a mammalian subject in need thereof.

Other methods, features and advantages of the present invention will be or become apparent to one with skill in the art upon examination of the following detailed descriptions. It is intended that all such additional methods, features and advantages be included within this description, be within the scope of the present invention, and be protected by the accompanying claims.

DETAILED DESCRIPTION OF THE INVENTION

Before the present compositions and methods are described, it is to be understood that the invention is not limited to the particular methodologies, protocols, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this invention belongs. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The term "nicotinic acetylcholine receptor" refers to the endogenous acetylcholine receptor having binding sites for acetylcholine which also bind to nicotine. The term "nicotinic acetylcholine receptor" includes the term "neural nicotinic acetylcholine receptor."

The terms "subtype of nicotinic acetylcholine receptor," and "nicotinic acetylcholine receptor subtype" refer to various subunit combinations of the nicotinic acetylcholine receptor, and may refer to a particular homomeric or heteromeric complex, or multiple homomeric or heteromeric complexes.

The term "agonist" refers to a substance which interacts with a receptor and increases or prolongs a physiological response (i.e. activates the receptor).

The term "partial agonist" refers to a substance which interacts with and activates a receptor to a lesser degree than an agonist.

The term "antagonist" refers to a substance which interacts with and decreases the extent or duration of a physiological response of that receptor.

The terms "disorder," "disease," and "condition" are used inclusively and refer to any status deviating from normal.

The term "central nervous system associated disorders" includes any cognitive, neurological, and mental disorders causing aberrant or pathological neural signal transmission, such as disorders associated with the alteration of normal neurotransmitter release in the brain.

The term "lower alkyl" refers to straight or branched chain alkyl radicals having in the range of 1 to 4 carbon atoms.

The term "alkyl" refers to straight or branched chain alkyl radicals having 1 to 19 carbon atoms, and "substituted alkyl" refers to alkyl radicals further bearing one or more substituents including, but not limited to, hydroxy, alkoxy (of a lower alkyl group), mercapto (of a lower alkyl group), aryl, heterocyclic, halogen, trifluoromethyl, cyano, nitro, amino, carboxyl, carbamate, sulfonyl, and sulfonamide.

The term "cycloalkyl" refers to cyclic ring-containing moieties containing 3 to 8 carbon atoms, and "substituted cycloalkyl" refers to cycloalkyl moieties further bearing one or more substituents as set forth above.

The term "alkenyl" refers to straight or branched chain hydrocarbyl groups having at least one carbon-carbon double bond and having 2 to 19 carbon atoms, and "substituted alkenyl" refers to alkenyl groups further bearing one or more substituents as set forth above.

The term "alkynyl" refers to straight or branched chain hydrocarbyl moieties having at least one carbon-carbon triple bond and having 2 to 19 carbon atoms, and "substituted alkynyl" refers to alkynyl moieties further bearing one or more substituents as set forth above.

The term "aryl" refers to aromatic groups having 6 to 24 carbon atoms, and "substituted aryl" refers to aryl groups further bearing one or more substituents as set forth above.

The term "heterocyclic" refers to cyclic moieties containing one or more heteroatoms as part of the ring structure and having 3 to 24 carbon atoms, and "substituted heterocyclic" refers to heterocyclic moieties further bearing one or more substituents as set forth above.

The term "halogen" refers to fluoride, chloride, bromide or iodide groups. It is understood that in all substituted groups defined above, polymers arrived at by defining substituents with further substituents to themselves (e.g. substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Compounds of the present invention are mono quaternary ammonium salts corresponding to Formula (I):

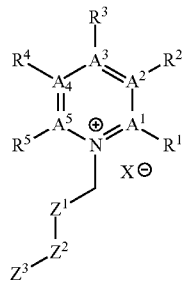

(I)

$A^1$, $A^2$, $A^3$, $A^4$, and $A^5$ are independently selected from nitrogen or carbon, provided that when nitrogen is present, the nitrogen does not have an R substituent attached.

$R^1$, $R^2$, $R^3$, $R^4$, and $R^5$ are each independently selected from the group consisting of hydrogen, alkyl, substituted alkyl, cycloalkyl, substituted cycloalkyl, alkenyl, substituted alkenyl, alkynyl, substituted alkynyl, aryl, substituted aryl, heterocycle, substituted heterocycle, halo, cyano, and nitro, or $R^1$ and $R^2$ or $R^2$ and $R^3$ together with the carbons to which they are attached independently form a three to eight-member cycloalkane, substituted cycloalkane, cycloalkene, substituted cycloalkene, aryl, substituted aryl, heterocycle with one to three hetero atoms in the ring, or substituted heterocycle with one to three hetero atoms in the ring.

$Z^1$ is absent or is selected from the group consisting of alkyl, substituted alkyl, cycloalkyl, substituted cycloalkyl, alkenyl, substituted alkenyl, alkynyl, substituted alkynyl, phenylene, substituted phenylene, alkoxy, and substituted alkoxy.

$Z^2$ is selected from the group consisting of alkyl, substituted alkyl, cycloalkyl, substituted cycloalkyl, alkenyl, substituted alkenyl, alkynyl, substituted alkynyl, arylene, substituted arylene, heterocycle, substituted heterocycle, alkoxy, and substituted alkoxy.

$Z^3$ is selected from is selected from hydrogen, alkyl, substituted alkyl, cycloalkyl, substituted cycloalkyl, alkenyl, substituted alkenyl, alkynyl, substituted alkynyl, aryl, substituted aryl, heterocycle, and substituted heterocycle.

$X^-$ is an inorganic or organic anion.

For example, $R^1$, $R^2$, $R^3$, $R^4$, and $R^5$ include hydrogen, methyl, ethyl, propyl, butyl, trifluoromethyl, pyrrolidine, N-alkyl pyrrolidine (for example where the alkyl chain is methyl, ethyl or propyl), unsaturated pyrrolidine, unsaturated N-alkyl pyrrolidine (for example where the alkyl chain is methyl, ethyl or propyl), aziridine, N-methyl aziridine, azetidine, N-methyl azetidine, unsaturated azetidine, unsaturated N-methyl azetidine, piperidine, N-methyl piperidine, unsaturated piperidine, unsaturated N-methyl piperidine, azepane, N-methyl azepane, unsaturated azepane, unsaturated N-methyl azepane, azocane, N-methyl azocane, unsaturated azocane, unsaturated N-methyl azocane, 1-aza-bicyclo[3.2.1]octane, 1-aza-bicyclo[2.2.1]heptane, 8-methyl-8-aza-bicyclo[3.2.1]octane, 1-aza-tricyclo[3.3.1.1$^{3,7}$]decane, methyl cycloalkyl, methyl substituted cycloalkyl, methylpyrrolidine, methyl N-alkyl pyrrolidine (for example where the alkyl chain is methyl, ethyl or propyl), methyl unsaturated pyrrolidine, methyl unsaturated N-alkyl pyrrolidine (for example where the alkyl chain is methyl, ethyl or propyl), methyl aziridine, methyl N-methyl aziridine, methyl azetidine, methyl N-methyl azetidine, methyl unsaturated azetidine, methyl unsaturated N-methyl azetidine, methyl piperidine, methyl N-methyl piperidine, methyl unsaturated piperidine, methyl unsaturated N-methyl piperidine, methyl azepane, methyl N-methyl azepane, methyl unsaturated azepane, methyl unsaturated N-methyl azepane, methyl azocane, methyl N-methyl azocane, methyl unsaturated azocane, methyl unsaturated N-methyl azocane, methyl-1-aza-bicyclo[3.2.1]octane, methyl-1-aza-bicyclo[2.2.1]heptane, 8-methyl-8-aza-bicyclo[3.2.1]octane, and methyl-1-aza-tricyclo[3.3.1.1$^{3,7}$]decane.

As another example, when $R^1$ and $R^2$, or $R^2$ and $R^3$ together with the carbons to which they are attached, independently form a three to eight-membered ring, that ring may be a heterocycle containing up to three hetero atoms (for example nitrogen, oxygen or sulfur) in the ring, and further may be substituted with one or more substituents. For example, possible rings include benzene, pyridine, pyran, indene, isoindene, benzofuran, isobenzofuran, benzo[b]thiophene, benzo[c]thiophene, indole, indolenine, isoindole, cyclopental[b]pyridine, pyrano[3,4-b]pyrrole, indazole, indoxazine, benzoxazole, anthranil naphthalene, tetralin, decalin, chromene, coumarin, chroman-4-one, isocoumarin, isochromen-3-one, quinoline, isoquinoline, cinnoline, quinazoline, naphthyridine, pyrido[3,4-b]-pyridine, pyridol[3,2-b]pyridine, pyrido[4,3-b]-pyridine, benzoxazine, anthracene, phenanthrene, phenalene, fluorene, carazole, xanthene, acnidine, octahydro-[1]pyridine, 1-methyloctahydro-[1]pyridine, octahydroindole, 1-methyloctahydro-indole, octahydro-cyclopenta[b]pyrrole, 1-methyloctahydro-cyclopenta[b]pyrrole, decahydroquinoline, or 1-methyldecahydroquinoline.

As a further example, heterocycles formed by $A^1$, $A^2$, $A^3$, $A^4$, and $A^5$ in combination with $R^1$, $R^2$, $R^3$, $R^4$, and $R^5$ include pyridine, quinoline, 5,6,7,8-tetrahydroquinoline, isoquinoline, tetrahydroisoquinoline, pyrazine, pyrimidine, pyridazine, and triazine, as well as substituted forms thereof.

$Z^1$ for example includes alkyl (for example butyl or pentyl), cis-alkenyl; trans-alkenyl; substituted cis-alkenyl; substituted trans-alkenyl; alkynyl (for example but-3-ynyl or pent-4-ynyl).

$Z^2$ for example includes cis-alkenyl, trans-alkenyl, substituted cis-alkenyl, and substituted trans-alkenyl.

$X^-$ for example includes Cl$^-$, Br$^-$, I$^-$, NO$_2^-$, HSO$_4^-$, SO$_4^-$, HPO$_4^-$, PO$_4^{2-}$, ethanesulfonate, trifluoromethane sulfate, p-toluenesulfonate, benzenesulfonate, salicylate, propionate, ascorbate, aspartate, fumarate, galactarate, maleate, citrate, glutamate, glycolate, lactate, malate, maleate, tartrate, oxalate, succinate, or similar pharmaceutically acceptable organic acid addition salts, including the pharmaceutically acceptable salts listed in the Journal of Pharmaceutical Sciences volume 66, page 2, 1977, which are hereby incorporated by reference. The above salt forms may be in some cases hydrates or solvates with alcohols and other solvents.

In a compound of Formula (I), preferably $A^1$, $A^2$, $A^3$, $A^4$, and $A^5$ are carbon.

In a compound of Formula (I), preferably $R^1$ is hydrogen, alkyl, or forms a six membered ring with $A^1$, $A^2$ and $R^2$ and with $R^1$ and $R^2$ providing four carbon atoms. More preferably, $R^1$ is selected from hydrogen, methyl, forms a six membered ring with $A^1$, $A^2$ and $R^2$ and with $R^1$ and $R^2$ providing four unsaturated carbon atoms, or forms a phenyl group with $A^1$, $A^2$ and $R^2$.

In a compound of Formula (I), preferably $R^2$ is hydrogen, alkyl, aryl, 3-hydroxypropyl, 1-methyl-2-pyrrolidinyl, halo, forms a six membered ring with $A^1$, $A^2$ and $R^1$ and with $R^1$ and $R^2$ providing four carbon atoms, or forms a six membered ring with $A^2$, $A^3$ and $R^3$ and with $R^2$ and $R^3$ providing four carbon atoms. More preferably, $R^2$ is hydrogen, methyl, ethyl, butyl, phenyl, 3-hydroxypropyl, 1-methyl-2-pyrrolidinyl, bromo, forms a six membered ring with $A^1$, $A^2$ and $R^1$ and with $R^1$ and $R^2$ providing four unsaturated carbon atoms, forms a phenyl group with $A^1$, $A^2$ and $R^1$, forms a six membered ring with $A^2$, $A^3$ and $R^3$ and with $R^2$ and $R^3$ providing four unsaturated carbon atoms, or forms a phenyl group with $A^2$, $A^3$ and $R^3$.

In a compound of Formula (I), preferably $R^3$ is hydrogen, alkyl, or forms a six membered ring with $A^2$, $A^3$ and $R^2$ and with $R^2$ and $R^3$ providing four carbon atoms. More preferably, $R^3$ is hydrogen, methyl, forms a six membered ring with $A^2$, $A^3$ and $R^2$ and with $R^2$ and $R^3$ providing four unsaturated carbon atoms, or forms a phenyl group with $A^2$, $A^3$ and $R^2$.

In a compound of Formula (I), preferably $R^4$ is hydrogen or alkyl. More preferably, $R^4$ is hydrogen or methyl.

In a compound of Formula (I), preferably $R^5$ is hydrogen.

In a compound of Formula (I), preferably $Z^1$ is absent, or is alkyl, alkynyl, or alkoxy. More preferably, $Z^1$ is absent, butyl, but-3-ynyl, pentyl, pent-4-ynyl or 2-ethoxy.

In a compound of Formula (I), preferably $Z^2$ is alkyl, arylenyl or alkoxy. More preferably, $Z^2$ is hexyl, octyl, dodecyl, tridecyl, para-phenylene, or 2-ethoxy.

In a compound of Formula (I), preferably $Z^3$ is alkyl, alkynyl, aryl or heterocyclic. More preferably, $Z^3$ is propyl, butyl, but-1-ynyl, hex-1-ynyl, phenyl, or 3-pyridinyl.

In a compound of Formula (I), preferably X is a halogen. More preferably, X is chloride, bromide or iodide.

In one embodiment, the compound of Formula (I) is defined wherein $A^1$, $A^2$, $A^3$, $A^4$, and $A^5$ are carbon; wherein $R^1$ is hydrogen, methyl, forms a six membered ring with $A^1$, $A^2$ and $R^2$ and with $R^1$ and $R^2$ providing four unsaturated carbon atoms, or forms a phenyl group with $A^1$, $A^2$ and $R^2$; wherein $R^2$ is hydrogen, methyl, ethyl, butyl, phenyl, 3-hydroxypropyl, 1-methyl-2-pyrrolidinyl, bromo, forms a six membered ring with $A^1$, $A^2$ and $R^1$ and with $R^1$ and $R^2$ providing four unsaturated carbon atoms, forms a phenyl group with $A^1$, $A^2$ and $R^1$, forms a six membered ring with $A^2$, $A^3$ and $R^3$ and with $R^2$ and $R^3$ providing four unsaturated carbon atoms, or forms a phenyl group with $A^2$, $A^3$ and $R^3$; wherein $R^3$ is hydrogen, methyl, forms a six membered ring with $A^2$, $A^3$ and $R^2$ and with $R^2$ and $R^3$ providing four unsaturated carbon atoms, or forms a phenyl group with $A^2$, $A^3$ and $R^2$; wherein $R^4$ is hydrogen or methyl; wherein $R^5$ is hydrogen; wherein $Z^1$ is absent, butyl, but-3-ynyl, pentyl, pent-4-ynyl or 2-ethoxy; wherein $Z^2$ is hexyl, octyl, dodecyl, tridecyl, para-phenylene, or 2-ethoxy; wherein $Z^3$ is propyl, butyl, but-1-ynyl, hex-1-ynyl, phenyl, or 3-pyridinyl; and wherein X is chloride, bromide or iodide.

In another embodiment, the compound of Formula (I) is defined wherein $A^1$, $A^2$, $A^3$, $A^4$, and $A^5$ are carbon; wherein $R^1$ is hydrogen, methyl, forms a six membered ring with $A^1$, $A^2$ and $R^2$ and with $R^1$ and $R^2$ providing four unsaturated carbon atoms, or forms a phenyl group with $A^1$, $A^2$ and $R^2$; wherein $R^2$ is hydrogen, methyl, ethyl, 3-hydroxypropyl, 1-methyl-2-pyrrolidinyl, bromo, forms a six membered ring with $A^1$, $A^2$ and $R^1$ and with $R^1$ and $R^2$ providing four unsaturated carbon atoms, forms a phenyl group with $A^1$, $A^2$ and $R^1$, forms a six membered ring with $A^2$, $A^3$ and $R^3$ and with $R^2$ and $R^3$ providing four unsaturated carbon atoms, or forms a phenyl group with $A^2$, $A^3$ and $R^3$; wherein $R^3$ is hydrogen, methyl, forms a six membered ring with $A^2$, $A^3$ and $R^2$ and with $R^2$ and $R^3$ providing four unsaturated carbon atoms, or forms a phenyl group with $A^2$, $A^3$ and $R^2$; wherein $R^4$ is hydrogen or methyl; wherein $R^5$ is hydrogen; wherein $Z^1$ is absent, butyl, but-3-ynyl, pent-4-ynyl or 2-ethoxy; wherein $Z^2$ is hexyl, octyl, dodecyl, tridecyl, para-phenylene, or 2-ethoxy; wherein $Z^3$ is propyl, butyl, but-1-ynyl, hex-1-ynyl, phenyl, or 3-pyridinyl; and wherein X is chloride, bromide or iodide.

In another embodiment, the compound of Formula (I) is defined wherein $A^1$, $A^2$, $A^3$, $A^4$, and $A^5$ are carbon; wherein $R^1$ is hydrogen, methyl, or forms a phenyl group with $A^1$, $A^2$ and $R^2$; wherein $R^2$ is hydrogen, methyl, butyl, phenyl, 1-methyl-2-pyrrolidinyl, forms a phenyl group with $A^1$, $A^2$ and $R^1$, or forms a phenyl group with $A^2$, $A^3$ and $R^3$; wherein $R^3$ is hydrogen, methyl, or forms a phenyl group with $A^2$, $A^3$ and $R^2$; wherein $R^4$ is hydrogen or methyl; wherein $R^5$ is hydrogen; wherein $Z^1$ is pentyl or pent-4-ynyl; wherein $Z^2$ is para-phenylene; wherein $Z^3$ is phenyl; and wherein X is bromide.

Exemplary compounds for this application are presented in Table 1.

TABLE 1

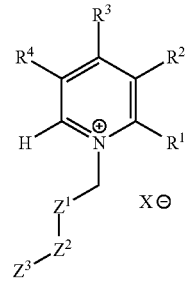

| ID # | $R^1$ | $R^2$ | $R^3$ | $R^4$ | $Z^1$ | $Z^2$ | $Z^3$ | X |
|---|---|---|---|---|---|---|---|---|
| GZ-565A | H | Me | H | H | but-3-ynyl | p-phenyl | phenyl | bromide |
| GZ-565B | Me | H | H | H | but-3-ynyl | p-phenyl | phenyl | bromide |
| GZ-565C | H | H | Me | H | but-3-ynyl | p-phenyl | phenyl | bromide |
| GZ-566A | H | Me | H | Me | but-3-ynyl | p-phenyl | phenyl | bromide |
| GZ-566B | H | Me | Me | H | but-3-ynyl | p-phenyl | phenyl | bromide |
| GZ-566C | Me | H | Me | H | but-3-ynyl | p-phenyl | phenyl | bromide |
| GZ-567A | phenyl with $R^2$ | phenyl with $R^1$ | H | H | but-3-ynyl | p-phenyl | phenyl | bromide |
| GZ-567B | H | phenyl with $R^3$ | phenyl with $R^2$ | H | but-3-ynyl | p-phenyl | phenyl | bromide |
| GZ-567C | H | 1-methyl-2-pyrrolidinyl | H | H | but-3-ynyl | p-phenyl | phenyl | bromide |
| GZ-568A | H | butyl | H | H | but-3-ynyl | p-phenyl | phenyl | bromide |

TABLE 1-continued

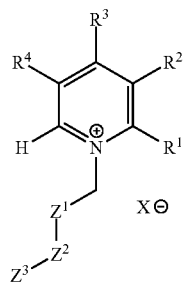

| ID # | R¹ | R² | R³ | R⁴ | Z¹ | Z² | Z³ | X |
|---|---|---|---|---|---|---|---|---|
| GZ-568B | H | phenyl | H | H | but-3-ynyl | p-phenyl | phenyl | bromide |
| GZ-568C | H | H | H | H | but-3-ynyl | p-phenyl | phenyl | bromide |
| GZ-573A | H | Me | H | H | butyl | p-phenyl | phenyl | bromide |
| GZ-573B | Me | H | H | H | butyl | p-phenyl | phenyl | bromide |
| GZ-573C | H | H | Me | H | butyl | p-phenyl | phenyl | bromide |
| GZ-574A | H | Me | H | Me | butyl | p-phenyl | phenyl | bromide |
| GZ-574B | H | Me | Me | H | butyl | p-phenyl | phenyl | bromide |
| GZ-574C | Me | H | Me | H | butyl | p-phenyl | phenyl | bromide |
| GZ-575A | phenyl with R¹ | phenyl with R¹ | H | H | butyl | p-phenyl | phenyl | bromide |
| GZ-575B | H | phenyl with R³ | phenyl with R² | H | butyl | p-phenyl | phenyl | bromide |
| GZ-575C | H | 1-methyl-2-pyrrolidinyl | H | H | butyl | p-phenyl | phenyl | bromide |
| GZ-576A | H | butyl | H | H | butyl | p-phenyl | phenyl | bromide |
| GZ-576B | H | H | H | H | butyl | p-phenyl | phenyl | bromide |
| ZZ-1-101 | H | 3-hydroxypropyl | H | H | propyl | p-phenyl | butyl | bromide |
| ZZ-1-104 | Me | H | H | H | propyl | p-phenyl | butyl | bromide |
| ZZ-1-107 | Me | H | Me | H | propyl | p-phenyl | butyl | bromide |
| ZZ-1-137A | H | Me | H | H | — | dodecyl | 3-pyridinyl | bromide |
| ZZ-1-137C | H | Me | H | Me | — | dodecyl | 3-pyridinyl | bromide |
| ZZ-1-137D | H | Me | Me | H | — | dodecyl | 3-pyridinyl | bromide |
| ZZ-1-137F | H | ring with R³, R² & R³ provide 4 unsaturated carbons | ring with R², R² & R³ provide 4 unsaturated carbons | H | — | dodecyl | 3-pyridinyl | bromide |
| ZZ-1-26 | H | H | Me | H | — | hexyl | hex-1-ynyl | iodide |
| ZZ-1-29 | H | 1-methyl-2-pyrrolidinyl | H | H | — | hexyl | hex-1-ynyl | iodide |
| ZZ-1-40A | H | Me | H | H | methoxy | 2-ethoxy | hexyl | chloride |
| ZZ-1-40B | H | H | Me | H | methoxy | 2-ethoxy | hexyl | chloride |
| ZZ-1-40C | H | Me | Me | H | methoxy | 2-ethoxy | hexyl | chloride |
| ZZ-1-40D | H | Me | H | Me | methoxy | 2-ethoxy | hexyl | chloride |
| ZZ-1-40E | Me | H | H | H | methoxy | 2-ethoxy | hexyl | chloride |
| ZZ-1-40F | Me | H | Me | H | methoxy | 2-ethoxy | hexyl | chloride |
| ZZ-1-40G | ring with R², R¹ & R² provide 4 unsaturated carbons | ring with R¹, R¹ & R² provide 4 unsaturated carbons | H | H | methoxy | 2-ethoxy | hexyl | chloride |
| ZZ-1-40H | H | ring with R³, R² & R³ provide 4 unsaturated carbons | ring with R², R² & R³ provide 4 unsaturated carbons | H | methoxy | 2-ethoxy | hexyl | chloride |
| ZZ-1-40I | H | 1-methyl-2-pyrrolidinyl | H | H | methoxy | 2-ethoxy | hexyl | chloride |
| ZZ-1-40J | H | hydroxypropyl | H | H | methoxy | 2-thoxy | hexyl | chloride |
| ZZ-1-47 | H | Me | H | H | — | heptyl | phenyl | bromide |
| ZZ-1-48 | H | H | Me | H | — | heptyl | phenyl | bromide |
| ZZ-1-49 | Me | H | H | H | — | heptyl | phenyl | bromide |
| ZZ-1-50 | Me | H | Me | H | — | heptyl | phenyl | bromide |
| ZZ-1-70 | H | Me | H | H | prop-2-ynyl | p-phenyl | butyl | bromide |
| ZZ-1-71 | H | H | Me | H | prop-2-ynyl | p-phenyl | butyl | bromide |
| ZZ-1-71A | H | Me | H | H | but-3-ynyl | p-phenyl | propyl | bromide |
| ZZ-1-71B | Me | H | H | H | but-3-ynyl | p-phenyl | propyl | bromide |
| ZZ-1-71C | H | H | Me | H | but-3-ynyl | p-phenyl | propyl | bromide |
| ZZ-1-71D | H | Me | Me | H | but-3-ynyl | p-phenyl | propyl | bromide |
| ZZ-1-71E | H | Me | H | Me | but-3-ynyl | p-phenyl | propyl | bromide |
| ZZ-1-71F | Me | H | Me | H | but-3-ynyl | p-phenyl | propyl | bromide |
| ZZ-1-71H | H | ring with R³, R² & R³ provide 4 unsaturated carbons | ring with R², R² & R³ provide 4 unsaturated carbons | H | but-3-ynyl | p-phenyl | propyl | bromide |
| ZZ-1-72 | H | Me | H | Me | prop-2-ynyl | p-phenyl | butyl | bromide |
| ZZ-1-73 | H | Me | Me | H | prop-2-ynyl | p-phenyl | butyl | bromide |
| ZZ-1-74 | H | ring with R³, R² & R³ provide 4 unsaturated carbons | ring with R², R² & R³ provide 4 unsaturated carbons | H | prop-2-ynyl | p-phenyl | butyl | bromide |
| ZZ-1-76 | H | Et | H | H | prop-2-ynyl | p-phenyl | butyl | bromide |
| ZZ-1-77 | H | hydroxypropyl | H | H | prop-2-ynyl | p-phenyl | butyl | bromide |
| ZZ-1-77A | H | Me | H | H | — | undecyl | 3-pyridinyl | bromide |
| ZZ-1-77B | H | H | [[H]]Me | H | — | undecyl | 3-pyridinyl | bromide |
| ZZ-1-77C | H | Br | H | H | — | undecyl | 3-pyridinyl | bromide |

TABLE 1-continued

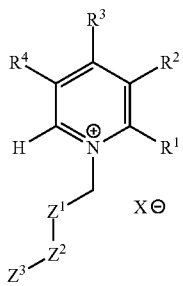

| ID # | R¹ | R² | R³ | R⁴ | Z¹ | Z² | Z³ | X |
|---|---|---|---|---|---|---|---|---|
| ZZ-1-77D | H | Me | Me | H | — | undecyl | 3-pyridinyl | bromide |
| ZZ-1-77E | H | Me | H | Me | — | undecyl | 3-pyridinyl | bromide |
| ZZ-1-77F | H | 1-methyl-2-pyrrolidinyl | H | H | — | undecyl | 3-pyridinyl | bromide |
| ZZ-1-94 | H | Me | H | H | propyl | p-phenyl | butyl | bromide |
| ZZ-1-95 | H | H | Me | H | propyl | p-phenyl | butyl | bromide |
| ZZ-1-96 | H | Me | H | Me | propyl | p-phenyl | butyl | bromide |
| ZZ-1-97 | H | Me | Me | H | propyl | p-phenyl | butyl | bromide |
| ZZ-1-98 | H | ring with R³, R² & R³ provide 4 unsaturated carbons | ring with R², R² & R³ provide 4 unsaturated carbons | H | propyl | p-phenyl | butyl | bromide |
| ZZU-1 | Me | H | H | H | — | hexyl | hex-1-ynyl | iodide |
| ZZU-2 | H | Me | H | H | — | hexyl | hex-1-ynyl | iodide |
| ZZU-3 | Me | H | Me | H | — | hexyl | hex-1-ynyl | iodide |
| ZZU-4 | H | Me | H | Me | — | hexyl | hex-1-ynyl | iodide |
| ZZU-5 | H | Me | Me | H | — | hexyl | hex-1-ynyl | iodide |
| ZZU-6 | Me | H | H | H | — | octyl | but-1-ynyl | bromide |
| ZZU-7 | H | Me | H | H | — | octyl | but-1-ynyl | bromide |
| ZZU-8 | H | H | Me | H | — | octyl | but-1-ynyl | bromide |

Exemplary compounds of the present invention include: 2-methyl-1-(8-phenyl-octyl)-pyridinium bromide; 3-methyl-1-(8-phenyl-octyl)-pyridinium bromide; 2,4-dimethyl-1-(8-phenyl-octyl)-pyridinium bromide; 4-methyl-1-(8-phenyl-octyl)-pyridinium bromide; 1-dodec-7-ynyl-2-methyl-pyridinium iodide; 1-dodec-7-ynyl-3-methyl-pyridinium iodide; 1-dodec-7-ynyl-4-methyl-pyridinium iodide; 1-dodec-7-ynyl-2,4-dimethyl-pyridinium iodide; 1-dodec-7-ynyl-3,5-dimethyl-pyridinium iodide; 1-dodec-7-ynyl-3,4-dimethyl-pyridinium iodide; 1-dodec-9-ynyl-2-methyl-pyridinium bromide; 1-dodec-9-ynyl-3-methyl-pyridinium bromide; 1-dodec-9-ynyl-4-methyl-pyridinium bromide; 1-[4-(4-butyl-phenyl)-butyl]-2-methyl-pyridinium bromide; 1-[4-(4-butyl-phenyl)-butyl]-3-methyl-pyridinium bromide; 1-[4-(4-butyl-phenyl)-butyl]-4-methyl-pyridinium bromide; 2-[4-(4-butyl-phenyl)-butyl]-5,6,7,8-tetrahydro-isoquinolinium bromide; 1-[4-(4-butyl-phenyl)-butyl]-3-(3-hydroxy-propyl)-pyridinium bromide; 1-[4-(4-butyl-phenyl)-butyl]-2,4-dimethyl-pyridinium bromide; 1-[4-(4-butyl-phenyl)-butyl]-3,4-dimethyl-pyridinium bromide; 1-[4-(4-butyl-phenyl)-butyl]-3,5-dimethyl-pyridinium bromide; 1-[4-(4-butyl-phenyl)-but-3-ynyl]-3-methyl-pyridinium bromide; 1-[4-(4-butyl-phenyl)-but-3-ynyl]-4-methyl-pyridinium bromide; 1-[4-(4-butyl-phenyl)-but-3-ynyl]-3-ethyl-pyridinium bromide; 2-[4-(4-butyl-phenyl)-but-3-ynyl]-5,6,7,8-tetrahydro-isoquinolinium bromide; 1-[4-(4-butyl-phenyl)-but-3-ynyl]-3,4-dimethyl-pyridinium bromide; 1-[4-(4-butyl-phenyl)-but-3-ynyl]-3,5-dimethyl-pyridinium bromide; 1-[4-(4-butyl-phenyl)-but-3-ynyl]-3-(3-hydroxy-propyl)-pyridinium bromide; 3-methyl-1-[13-(3-pyridinyl)-tridecyl]-pyridinium bromide; 3,4-dimethyl-1-[13-(3-pyridinyl)-tridecyl]-pyridinium bromide; 3,5-dimethyl-1-[13-(3-pyridinyl)-tridecyl]-pyridinium bromide; 2-[13-(3-pyridinyl)-tridecyl]-5,6,7,8-tetrahydro-isoquinolinium bromide; 1-[5-(1,1'-biphenyl-4-yl)-pent-4-ynyl]-2-methyl-pyridinium bromide; 1-[5-(1,1'-biphenyl-4-yl)-pent-4-ynyl]-3-methyl-pyridinium bromide; 1-[5-(1,1'-biphenyl-4-yl)-pent-4-ynyl]-4-methyl-pyridinium bromide; 1-[5-(1,1'-biphenyl-4-yl)-pent-4-ynyl]-2,4-dimethyl-pyridinium bromide; 1-[5-(1,1'-biphenyl-4-yl)-pent-4-ynyl]-3,4-dimethyl-pyridinium bromide; 1-[5-(1,1'-biphenyl-4-yl)-pent-4-ynyl]-3,5-dimethyl-pyridinium bromide; 1-[5-(1,1'-biphenyl-4-yl)-pent-4-ynyl]-quinolinium bromide; 2-[5-(1,1'-biphenyl-4-yl)-pent-4-ynyl]-isoquinolinium bromide; 1-[5-(1,1'-biphenyl-4-yl)-pent-4-ynyl]-3-butyl-pyridinium bromide; 1-[5-(1,1'-biphenyl-4-yl)-pent-4-ynyl]-3-phenyl-pyridinium bromide; 1-[5-(1,1'-biphenyl-4-yl)-pent-4-ynyl]-1-pyridinium bromide; 1-[5-(1,1'-biphenyl-4-yl)-pentyl]-2-methyl-pyridinium bromide; 1-[5-(1,1'-biphenyl-4-yl)-pentyl]-3-methyl-pyridinium bromide; 1-[5-(1,1'-biphenyl-4-yl)-pentyl]-4-methyl-pyridinium bromide; 1-[5-(1,1'-biphenyl-4-yl)-pentyl]-2,4-dimethyl-pyridinium bromide; 1-[5-(1,1'-biphenyl-4-yl)-pentyl]-3,4-dimethyl-pyridinium bromide; 1-[5-(1,1'-biphenyl-4-yl)-pentyl]-3,5-dimethyl-pyridinium bromide; 1-[5-(1,1'-biphenyl-4-yl)-pentyl]-quinolinium bromide; 2-[5-(1,1'-biphenyl-4-yl)-pentyl]-isoquinolinium bromide; 1-[5-(1,1'-biphenyl-4-yl)-pentyl]-3-butyl-pyridinium bromide; 1-[5-(1,1'-biphenyl-4-yl)-pentyl]-pyridinium bromide; 1-dodec-7-ynyl-3-(1-methyl-2-pyrrolidinyl)-pyridinium iodide; 3-methyl-1-[4-(4-propyl-phenyl)-pent-4-ynyl]-pyridinium bromide; 2-methyl-1-[4-(4-propyl-phenyl)-pent-4-ynyl]-pyridinium bromide; 4-methyl-1-[4-(4-propyl-phenyl)-pent-4-ynyl]-pyridinium bromide; 3,4-dimethyl-1-[4-(4-propyl-phenyl)-pent-4-ynyl]-pyridinium bromide; 3,5-dimethyl-1-[4-(4-propyl-phenyl)-pent-4-ynyl]-pyridinium bromide; 2,4-dimethyl-1-[4-(4-propyl-phenyl)-pent-4-ynyl]-pyridinium bromide; 2-[4-(4-propyl-phenyl)-pent-4-ynyl]-5,6,7,8-tetrahydro-isoquinolinium bromide; 1-[5-(1,1'-biphenyl-4-yl)-pent-4-ynyl]-3-(1-methyl-2-pyrrolidinyl)-pyridinium bromide;

1-[5-(1,1'-biphenyl-4-yl)-pentyl]-3-(1-methyl-2-pyrrolidinyl)-pyridinium bromide; 1-[2-(2-hexoxy-ethoxy)-ethyl]-3-methyl-pyridinium chloride; 1-[2-(2-hexoxy-ethoxy)-ethyl]-4-methyl-pyridinium chloride; 1-[2-(2-hexoxy-ethoxy)-ethyl]-3,4-dimethyl-pyridinium chloride; 1-[2-(2-hexoxy-ethoxy)-ethyl]-3,5-dimethyl-pyridinium chloride; 1-[2-(2-hexoxy-ethoxy)-ethyl]-2-methyl-pyridinium chloride; 1-[2-(2-hexoxy-ethoxy)-ethyl]-2,4-dimethyl-pyridinium chloride; 1-[2-(2-hexoxy-ethoxy)-ethyl]-5,6,7,8-tetrahydro-quinolinium chloride; 2-[2-(2-hexoxy-ethoxy)-ethyl]-5,6,7,8-tetrahydro-isoquinolinium chloride; 1-[2-(2-hexoxy-ethoxy)-ethyl]-3-methyl-pyridinium chloride; 1-[2-(2-hexoxy-ethoxy)-ethyl]-3-methyl-pyridinium chloride; 3-methyl-1-[12-(3-pyridinyl)-dodecyl]-pyridinium bromide; 4-methyl-1-[12-(3-pyridinyl)-dodecyl]-pyridinium bromide; 3-bromo-1-[12-(3-pyridinyl)-dodecyl]-pyridinium bromide; 3,4-dimethyl-1-[12-(3-pyridinyl)-dodecyl]-pyridinium bromide; 3,5-dimethyl-1-[12-(3-pyridinyl)-dodecyl]-pyridinium bromide; and 3-(1-methyl-2-pyrrolidinyl)-1-[12-(3-pyridinyl)-dodecyl]-pyridinium bromide.

The compounds of the present invention may contain one or more stereocenters. The invention includes all possible diastereomers and all enantiomeric forms as well as racemic mixtures. The compounds can be separated into substantially optically pure compounds.

The compounds of the invention are nicotinic acetylcholine receptor agents. Thus, they may augment or inhibit [$^3$H]nicotine binding, [$^3$H]MLA binding, evoke or inhibit neurotransmitter release, and/or evoke or inhibit the flux of ions through the nicotinic receptor.

In one embodiment, the present invention relates to a method for selectively modulating the function of a nicotinic acetylcholine receptor comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agonist or partial agonist of nicotinic acetylcholine receptor function. Hence the compound of Formula (I) may increase or prolong the release of a neurotransmitter from a central nervous system tissue. The neurotransmitter affected may include dopamine, norepinephrine, serotonin, gamma-aminobutyric acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue. The neurotransmitter affected may include dopamine, norepinephrine, serotonin, gamma-aminobutyric acid, or glutamate.

In another embodiment, the present invention is directed to a method for preventing and/or treating a central nervous system associated disorder comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agonist or partial agonist of nicotinic acetylcholine receptor function. Hence the compound of Formula (I) may increase or prolong the release of a neurotransmitter from a central nervous system tissue. The neurotransmitter affected may include dopamine, norepinephrine, serotonin, gamma-aminobutyric acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue. The neurotransmitter affected may include dopamine, norepinephrine, serotonin, gamma-aminobutyric acid, or glutamate.

Central nervous system disorders which may be treated according to the method of the present invention include Alzheimer's disease, dementia, cognitive dysfunctions (including disorders of attention, focus and concentration), attention deficit disorders, affective disorders, extrapyramidal motor function disorders, Parkinson's disease, progressive supramolecular palsy, Huntington's disease, Gilles de la Tourette syndrome, tardive dyskinesia, neuroendocrine disorders, dysregulation of food intake, disorders of nociception, pain, mood and emotional disorders, depression, panic anxiety, psychosis, schizophrenia, or epilepsy.

In yet another embodiment, the present invention is directed to a method for preventing and/or treating substance use and/or abuse comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agonist or partial agonist of nicotinic acetylcholine receptor function. Hence the compound of Formula (I) may increase or prolong the release of a neurotransmitter from a central nervous system tissue. The neurotransmitter affected may include dopamine, norepinephrine, serotonin, gamma-aminobutyric acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue. The neurotransmitter affected may include dopamine, norepinephrine, serotonin, gamma-aminobutyric acid, or glutamate.

The conditions of substance use and/or abuse treated according to the method of the present invention include nicotine abuse (including use in smoking cessation therapy), nicotine intoxication, amphetamine abuse, methamphetamine abuse, cocaine abuse, or alcohol abuse.

In another embodiment, the present invention is directed to a method for preventing and/or treating gastrointestinal tract disorders comprising administering to a mammalian subject in need thereof a therapeutically effective amount of a compound of Formula (I). In such a method, the compound of Formula (I) may selectively bind to one or more subtypes of nicotinic acetylcholine receptor. The compound of Formula (I) may act as an agonist or partial agonist of nicotinic acetylcholine receptor function. Hence the compound of Formula (I) may increase or prolong the release of a neurotransmitter from a central nervous system tissue. The neurotransmitter affected may include dopamine, norepinephrine, serotonin, gamma-aminobutyric acid, or glutamate. Alternatively, the compound of Formula (I) may act as an antagonist of nicotinic acetylcholine receptor function. Hence the compound of Formula (I) may decrease the extent or duration of the release of a neurotransmitter from a central nervous system tissue. The neurotransmitter affected may include dopamine, norepinephrine, serotonin, gamma-aminobutyric acid, or glutamate.

Gastrointestinal disorders which may be treated according to the method of the present invention include irritable bowel syndrome, colitis, diarrhea, constipation, gastric acid secretion or ulcers.

The compounds of the present invention can be delivered directly or in pharmaceutical compositions along with suitable carriers or excipients, as is well known in the art. For example, a pharmaceutical composition of the invention may include a conventional additive, such as a stabilizer, buffer, salt, preservative, filler, flavor enhancer and the like, as known to those skilled in the art. Exemplary buffers include phosphates, carbonates, citrates and the like. Exemplary preservatives include EDTA, EGTA, BHA, BHT and the like.

An effective amount of such agents can readily be determined by routine experimentation, as can the most effective and convenient route of administration and the most appropriate formulation. Various formulations and drug delivery systems are available in the art. See, e.g., Gennaro, A. R., ed. (1995) Remington's Pharmaceutical Sciences.

Suitable routes of administration may, for example, include oral, rectal, transmucosal, nasal, or intestinal administration and parenteral delivery, including intramuscular, subcutaneous, intramedullary injections, as well as intrathecal, direct intraventricular, intravenous, intraperitoneal, intranasal, or intraocular injections. The agent or composition thereof may be administered in a local rather than a systemic manner. For example, a suitable agent can be delivered via injection or in a targeted drug delivery system, such as a depot or sustained release formulation.

The pharmaceutical compositions of the present invention may be manufactured by any of the methods well-known in the art, such as by conventional mixing, dissolving, granulating, dragee-making, levigating, emulsifying, encapsulating, entrapping, or lyophilizing processes. As noted above, the compositions of the present invention can include one or more physiologically acceptable carriers such as excipients and auxiliaries that facilitate processing of active molecules into preparations for pharmaceutical use.

Proper formulation is dependent upon the route of administration chosen. For injection, for example, the composition may be formulated in aqueous solutions, preferably in physiologically compatible buffers such as Hanks' solution, Ringer's solution, or physiological saline buffer. For transmucosal or nasal administration, penetrants appropriate to the barrier to be permeated are used in the formulation. Such penetrants are generally known in the art. In a preferred embodiment of the present invention, the present compounds are prepared in a formulation intended for oral administration. For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject. The compounds may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Also, wetting agents such as sodium dodecyl sulfate may be included.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In one embodiment, the compounds of the present invention can be administered transdermally, such as through a skin patch, or topically. In one aspect, the transdermal or topical formulations of the present invention can additionally comprise one or multiple penetration enhancers or other effectors, including agents that enhance migration of the delivered compound. Transdermal or topical administration could be preferred, for example, in situations in which location specific delivery is desired.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, for example, gelatin, for use in an inhaler or insufflator may be formulated. These typically contain a powder mix of the compound and a suitable powder base such as lactose or starch.

Compositions formulated for parenteral administration by injection, e.g., by bolus injection or continuous infusion can be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Formulations for parenteral administration include aqueous solutions or other compositions in water-soluble form.

Suspensions of the active compounds may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

As mentioned above, the compositions of the present invention may also be formulated as a depot preparation. Such long acting formulations may be administered by implantation (for example, subcutaneously or intramuscularly) or by intramuscular injection. Thus, for example, the present compounds may be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well known in the art and include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system is effective in dissolving hydrophobic compounds and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also may be employed, although usually at the cost of greater toxicity. Additionally, the compounds may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the compounds for a few weeks up to over 100 days. Depending on the chemical nature and the biological stability of the therapeutic reagent, additional strategies for stabilization may be employed.

For any composition used in the present methods of treatment, a therapeutically effective dose can be estimated initially using a variety of techniques well known in the art. For example, in a cell culture assay, a dose can be formulated in animal models to achieve a circulating concentration range that includes the $IC_{50}$ as determined in cell culture. Dosage ranges appropriate for human subjects can be determined, for example, using data obtained from cell culture assays and other animal studies.

A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein, and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications fall within the scope of the appended claims.

Example 1

Synthesis of compound
2-methyl-1-(8-phenyl-octyl)-pyridinium bromide

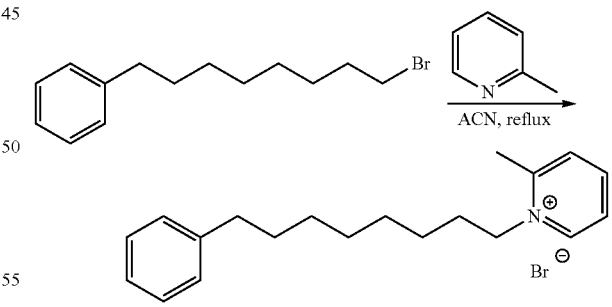

(8-Bromo-octyl)-benzene (1 mmol) was added to a solution of 2-picoline (3 mmol) in acetonitrile, and the solution mixture was refluxed for 24 hours. The acetonitrile was removed in a vacuum, and the resulting residue was partitioned between ether and water. The aqueous layer was washed extensively with ether until no picoline was left in the aqueous layer. The resulting aqueous solution of the product was extracted with chloroform. The chloroform was removed to afford the product (70%). $^1$HNMR (300 MHz, CDCl3, ppm) 9.74 (d, 1H), 8.35 (m, 1H), 7.96 (m, 1H), 7.86

(d, 1H), 7.15-7.25 (m, 4H), 4.92 (t, 2H), 2.95 (s, 3H), 1.88-1.98 (m, 2H), 1.54-1.64 (m, 2H), 1.39-1.49 (m, 2H), 1.25-1.38 (br, 6H).

Example 2

Synthesis of compound
3-methyl-1-(8-phenyl-octyl)-pyridinium bromide

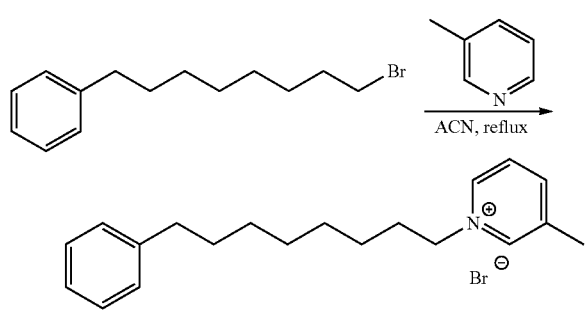

(8-Bromo-octyl)-benzene (1 mmol) was added to a solution of 3-picoline (3 mmol) in acetonitrile, and the solution refluxed for 24 hours. The acetonitrile was removed in a vacuum and the resulting residue was partitioned between ether and water. The aqueous layer was washed extensively with ether until no picoline was left in the aqueous layer. The resulting aqueous solution of the product was extracted with chloroform. The chloroform was removed to afford the product (76%). $^1$HNMR (300 MHz, CDCl3, ppm) 9.40 (s, 1H), 9.22 (d, 1H), 8.02 (d, 1H), 7.96 (dd, 1H), 7.12-7.22 (dd, 4H), 4.94 (t, 2H), 2.62 (s, 3H), 2.56 (t, 2H), 1.94-2.04 (m, 2H), 1.50-1.60 (m, 2H), 1.20-1.40 (br, 8H). $^{13}$CNMR, 145.68, 144.65, 142.87, 142.37, 139.79, 128.55, 128.40, 127.89, 125.76, 62.20, 36.19, 32.29, 31.73, 29.53, 29.44, 29.33, 26.40, 19.11.

Example 3

Synthesis of compound
2,4-dimethyl-1-(8-phenyl-octyl)-pyridinium bromide

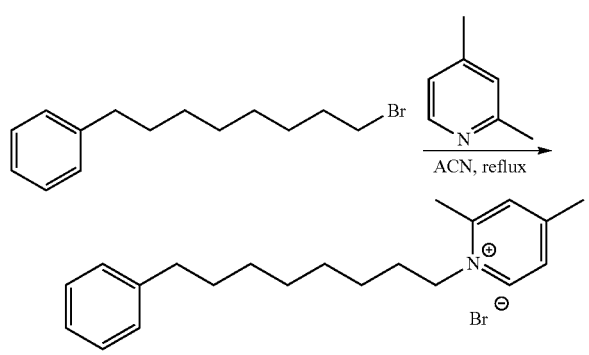

(8-Bromo-octyl)-benzene (1 mmol) was added to a solution of 2,4-lutidine (3 mmol) in acetonitrile, and the solution refluxed for 24 hours. The acetonitrile was removed in a vacuum and the resulting residue was partitioned between ether and water. The aqueous layer was washed extensively with ether until no 2,4-lutidine was left in the aqueous layer. The resulting aqueous solution of the product was extracted with chloroform. The chloroform was removed to afford the product (70%). $^1$HNMR (300 MHz, CDCl3, ppm), 9.50 (d, 1H), 7.70 (d, 1H), 7.60 (s, 1H), 7.10-7.30 (dd, 1H), 4.78 (t, 2H), 2.84 (s, 3H), 2.54-2.60 (m, 5H), 1.80-1.92 (m, 2H), 1.50-1.60 (br, 2H), 1.20-1.45 (br, 6H).

Example 4

Synthesis of compound
4-methyl-1-(8-phenyl-octyl)-pyridinium bromide

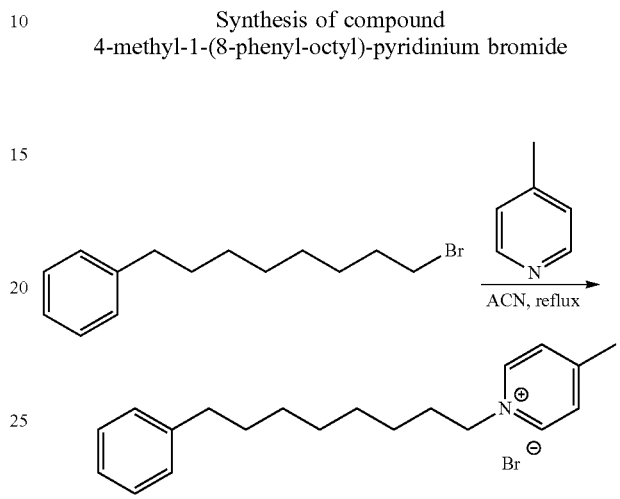

(8-Bromo-octyl)-benzene (1 mmol) was added to a solution of 4-picoline (3 mmol) in acetonitrile, and the solution was refluxed for 24 hours. The acetonitrile was removed in vacuum and the resulting residue was partitioned between ether and water. The aqueous layer was washed extensively with ether until no picoline was left in the aqueous layer. The resulting aqueous solution of the product was extracted with chloroform. The chloroform was removed to afford the product (78%). $^1$HNMR (300 MHz, CDCl3, ppm) 9.26 (d, 2H), 7.84 (d, 2H), 7.14-7.28 (dd, 4H), 4.90 (t, 2H), 2.62 (s, 3H), 2.56 (t, 2H), 1.92-2.02 (m, 2H), 1.50-1.60 (m, 2H), 1.20-1.40 (br, 8H). $^{13}$CNMR, 158.92, 144.28, 142.86, 128.95, 128.56, 128.40, 125.76, 61.61, 36.19, 32.15, 31.71, 29.53, 29.42, 29.31, 26.37, 22.63.

Example 5

Synthesis of compound
1-dodec-7-ynyl-2-methyl-pyridinium iodide

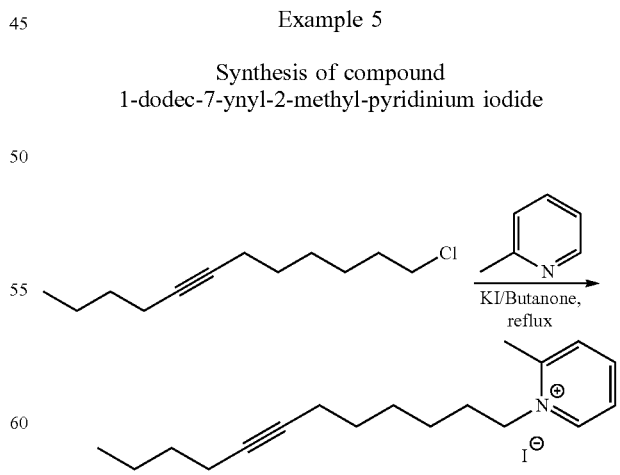

12-Chloro-dodec-5-yne (1 mmol) was mixed with potassium iodide (3 mmol) and 2-picoline (3 mmol) in butanone. room temperature. The butanone was removed in a vacuum, and the resulting residue was partitioned between water and ethyl ether. The aqueous layer was washed extensively with ether until no 2-picoline was left in the aqueous layer. The resulting aqueous solution of the product was extracted with chloroform. The chloroform was removed to afford the product (85%). $^1$HNMR (300 MHz, CDCl3, ppm) 9.62 (d, 1H), 8.39 (dd, 1H), 7.99 (m, 1H), 7.91 (d, 1H), 4.88 (t, 2H), 2.97 (s, 3H), 2.12-2.20 m, 4H), 1.90-2.00 (m, 2H), 1.32-1.58 (m, 8H), 0.88 (t, 3H).

Example 6

Synthesis of compound
1-dodec-7-ynyl-3-methyl-pyridinium iodide

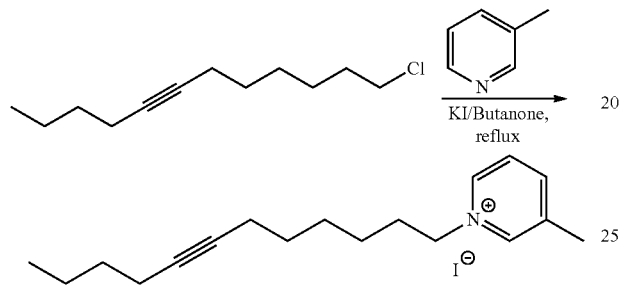

12-Chloro-dodec-5-yne (1 mmol) was mixed with potassium iodide (3 mmol) and 3-picoline (3 mmol) in butanone. The mixture was refluxed for 3 days and cooled to room temperature, filtrated. The butanone was removed in a vacuum, and the resulting residue was partitioned between water and ethyl ether. The aqueous layer was washed extensively with ether until no 3-picoline was left in the aqueous layer. The resulting aqueous solution of the product was extracted with chloroform. The chloroform was removed to afford the product (82%). $^1$HNMR (300 MHz, CDCl3, ppm) 9.36 (s, 1H), 9.18 (d, 1H), 8.24 (d, 1H), 8.00 (dd, 1H), 4.92 (t, 2H), 2.62 (s, 3H), 1.95-2.18 (m, 6H), 1.15-1.25 (br, 10H), 0.90 (t, 3H); $^{13}$CNMR, 145.51, 144.12, 144.78, 139.46, 127.56, 80.44, 79.42, 61.75, 31.72, 31.16, 28.65, 28.04, 25.52, 21.92, 18.75, 18.55, 18.40, 13.63.

Example 7

Synthesis of compound
1-dodec-7-ynyl-4-methyl-pyridinium iodide

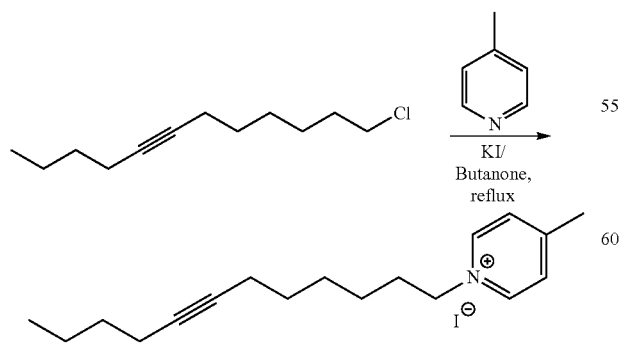

12-Chloro-dodec-5-yne (1 mmol) was mixed with potassium iodide (3 mmol) and 4-picoline (3 mmol) in butanone. The mixture was refluxed for 3 days and cooled to room temperature, filtrated. The butanone was removed in a vacuum, and the resulting residue was partitioned between water and ethyl ether. The aqueous layer was washed extensively with ether until no 4-picoline was left in the aqueous layer. The resulting aqueous solution of the product was extracted with chloroform. The chloroform was removed to afford the product (87%). $^1$HNMR (300 MHz, CDCl3, ppm), 9.28 (d, 2H), 7.92 (d, 2H), 4.92 (t, 2H), 2.68 (s, 3H), 1.96-2.18 (m, 6H), 1.32-1.50 (br, 10H), 0.88 (t, 3H).

Example 8

Synthesis of compound
1-dodec-7-ynyl-2,4-dimethyl-pyridinium iodide

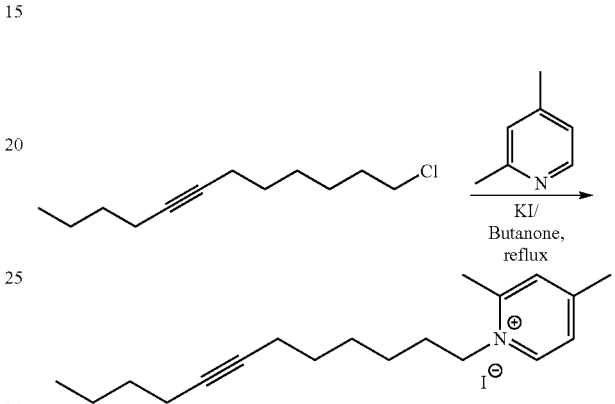

12-Chloro-dodec-5-yne (1 mmol) was mixed with potassium iodide (3 mmol) and 2,4-lutidine (3 mmol) in butanone. The mixture was refluxed for 3 days and cooled to room temperature, filtrated. The butanone was removed in a vacuum, and the resulting residue was partitioned between water and ethyl ether. The aqueous layer was washed extensively with ether until no 2,4-lutidine was left in the aqueous layer. The resulting aqueous solution of the product was extracted with chloroform. The chloroform was removed to afford the product (84%). $^1$HNMR (300 MHz, CDCl3, ppm), 9.40 (d, 1H), 7.75 (d, 1H), 7.66 (s, 1H), 4.78 (t, 3H), 2.88 (s, 3H), 2.60 (s, 3H), 2.05-2.15 (br, 4H), 1.80-2.00 (br, 2H), 1.30-1.50 (br, 10H), 0.86 (t, 3H); $^{13}$CNMR, 156.73, 153.05, 145.84, 136.61, 127.27, 80.86, 79.85, 58.12, 31.54, 30.94, 39.09, 26.17, 22.39, 22.30, 21.03, 18.96, 18.79, 14.02.

Example 9

Synthesis of compound
1-dodec-7-ynyl-3,5-dimethyl-pyridinium iodide

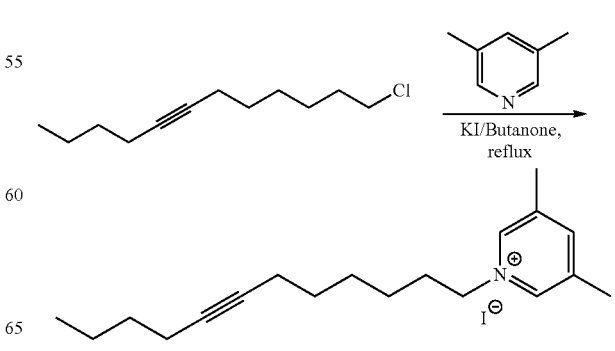

12-Chloro-dodec-5-yne (1 mmol) was mixed with potassium iodide (3 mmol) and 3,5-lutidine (3 mmol) in butanone. The mixture was refluxed for 3 days and cooled to room temperature, filtrated. The butanone was removed in vacuum, and the resulting residue was partitioned between water and ethyl ether. The aqueous layer was washed extensively with ether until no 3,5-lutidine was left in the aqueous layer. The resulting aqueous solution of the product was extracted with chloroform. The chloroform was removed to afford the product (78%). ¹HNMR (300 MHz, CDCl3, ppm), 9.06 (s, 2H), 8.00 (s, 1H), 4.86 (t, 3H), 2.48 (s, 3H), 1.98-2.16 (m, 6H), 1.32-1.48 (br, 10H), 0.88 (t, 3H); ¹³CNMR, 146.12, 141.38, 138.64, 80.43, 79.53, 61.46, 31.70, 31.17, 28.68, 28.07, 25.55, 21.92, 18.57, 18.42, 13.63.

Example 10

Synthesis of compound
1-dodec-7-ynyl-3,4-dimethyl-pyridinium iodide

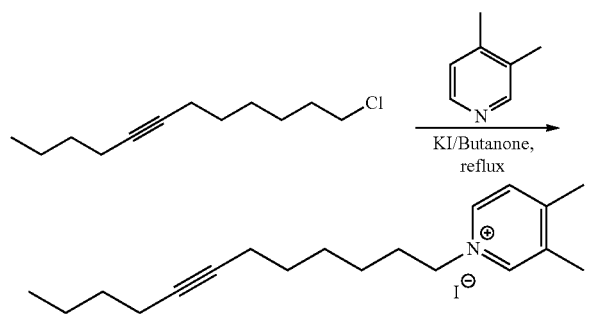

12-Chloro-dodec-5-yne (1 mmol) was mixed with Sodium iodide (3 mmol) and 3,4-lutidine (3 mmol) in butanone. The mixture was refluxed for 3 days and cooled to room temperature, filtrated. The butanone was removed in vacuum, and the resulting residue was partitioned between water and ethyl ether. The aqueous layer was washed extensively with ether until no 3,4-lutidine was left in the aqueous layer. The resulting aqueous solution of the product was extracted with chloroform. The chloroform was removed to afford the product (72%). ¹HNMR, (300 MHz, CDCl3, ppm, ppm), 9.22 (s, 1H), 9.04 (d, 1H), 7.80 (d, 1H), 4.84 (t, 3H), 2.52 (s, 3H), 2.50 (s, 3H), 1.92-2.14 (m, 6H), 1.28-1.45 (m, 10H), 0.84 (t, 3H). ¹³CNMR, 157.84, 143.39, 141.81, 138.53, 128.72, 80.80, 79.90, 61.23, 32.03, 31.54, 29.08, 28.48, 25.91, 22.30, 20.78, 18.96, 18.79, 17.44, 14.02.

Example 11

Synthesis of 1-dodec-9-ynyl-2-methyl-pyridinium bromide

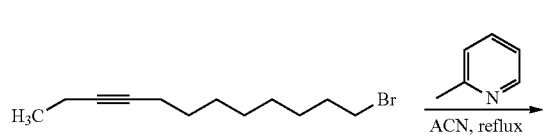

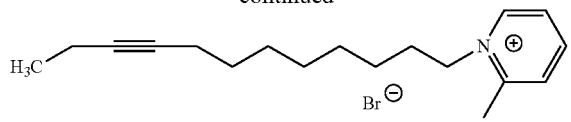

12-Bromo-dodec-3-yne (1 mmol) was added to a solution of 2-picoline (3 mmol) in acetonitrile, and the solution was refluxed for 24 hours. The acetonitrile was removed in vacuum, and the resulting residue was partitioned between ether and water. The aqueous layer was washed extensively with ether until no 2-picoline was left in the aqueous layer. The resulting aqueous solution of the product was extracted with chloroform. The chloroform was removed to afford the product (70%). ¹HNMR (300 MHz, CDCl3, ppm), 9.68 (d, 1H), 8.28 (m, 1H), 7.96 (m, 1H), 7.84 (d, 1H), 4.94 (t, 2H), 2.98 (s, 3H), 2.05-2.20 (m, 4H), 1.88-2.00 (m, 2H), 1.20-1.60 (br, 10H), 1.10 (t, 3H).

Example 12

Synthesis of compound
1-dodec-9-ynyl-3-methyl-pyridinium bromide

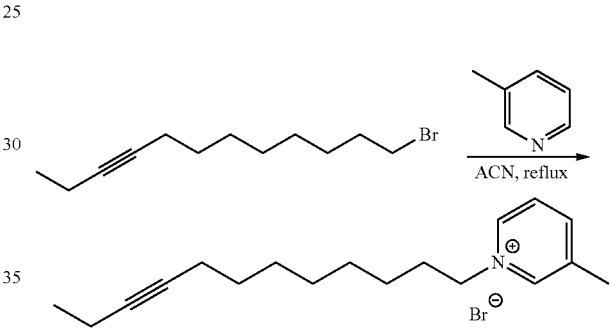

12-Bromo-dodec-3-yne (1 mmol) was added to a solution of 3-picoline (3 mmol) in acetonitrile, and the solution was refluxed for 24 hours. The acetonitrile was removed in a vacuum, and the resulting residue was partitioned between ether and water. The aqueous layer was washed extensively with ether until no picoline was left in the aqueous layer. The resulting aqueous solution of the product was extracted with chloroform. The chloroform was removed to afford the product (70%). ¹HNMR (300 MHz, CDCl3, ppm), 9.42 (s, 1H), 9.24 (d, 1H), 8.24 (d, 1H), 8.00 (dd, 1H), 4.95 (t, 2H), 2.62 (s, 3H), 1.95-2.2 (m, 6H), 1.23-1.45 (br, 10H), 1.1 (t, 3H); ¹³CNMR, 145.29, 144.24, 141.98, 139.42, 127.51, 81.57, 79.26, 61.83, 31.90, 28.95, 28.92, 28.82, 28.62, 26.02, 18.72, 18.63, 14.38, 12.40.

Example 13

Synthesis of compound
1-dodec-9-ynyl-4-methyl-pyridinium bromide

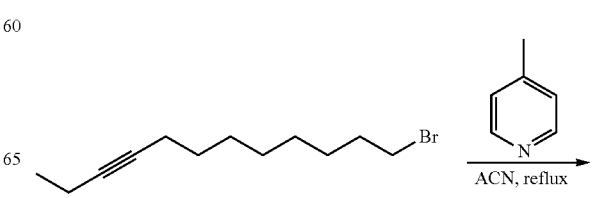

-continued

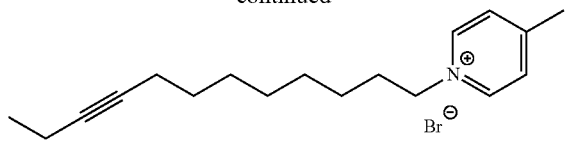

12-Bromo-dodec-3-yne (1 mmol) was added to a solution of 4-picoline (3 mmol) in acetonitrile, and the solution was refluxed for 24 hours. The acetonitrile was removed in a vacuum, and the resulting residue was partitioned between ether and water. The aqueous layer was washed extensively with ether until no picoline was left in the aqueous layer. The resulting aqueous solution of the product was extracted with chloroform. The chloroform was removed to afford the product (82%). $^1$HNMR (300 MHz, CDCl3, ppm), 9.24 (d, 2H), 7.86 (d, 2H), 4.90 (t, 2H), 2.64 (s, 3H), 1.95-2.16 (m, 6H), 1.26-1.34 (br, 10H), 0.88 (t, 3H).

Example 14

Synthesis of 1-[4-(4-butyl-phenyl)-butyl]-2-methyl-pyridinium bromide

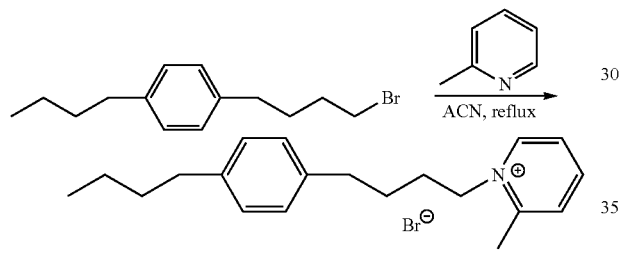

1-(4-Bromo-butyl)-4-butyl-benzene (1 mmol) was added to a solution of 2-picoline (3 mmol) in acetonitrile, and the solution was refluxed for 24 hours. The acetonitrile was removed in a vacuum, and the resulting residue was partitioned between ether and water. The aqueous layer was washed extensively with ether until no 2-picoline was left in the aqueous layer. The resulting aqueous solution of the product was extracted with chloroform. The chloroform was removed to afford the product (74%). $^1$HNMR (300 MHz, CDCl3, ppm), 9.69 (d, J=6.6, 1H), 8.25-8.30 (m, 1H), 7.90-7.95 (m, 1H), 7.77 (d, J=7.8, 1H), 7.04-7.10 (m, 4H), 4.92 (t, 7.5, 2H), 2.84 (s, 3H), 2.66 (t, J=7.2, 2H), 2.56 (t, J=7.5, 2H), 1.89-1.98 (m, 2H), 1.78-1.86 (m, 2H), 1.51-1.59 (m, 2H), 1.27-1.37 (m, 2H), 0.91 (t, J=7.2, 3H).

Example 15

Synthesis of compound 1-[4-(4-butyl-phenyl)-butyl]-3-methyl-pyridinium bromide

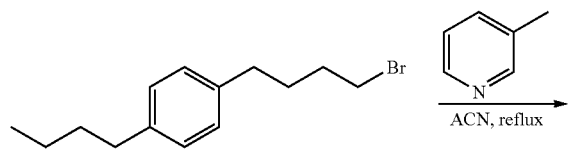

-continued 1-(4-Bromo-butyl)-4-butyl-benzene (1 mmol) was added to a solution of 3-picoline (3 mmol) in acetonitrile and the solution refluxed for 24 hours. The acetonitrile was removed in vacuum, and the resulting residue was partitioned between ether and water. The aqueous layer was washed extensively with ether until no picoline was left in the aqueous layer. The resulting aqueous solution of the product was extracted with chloroform. The chloroform was removed to afford the product (75%). $^1$HNMR (300 MHz, CDCl3, ppm), 9.32 (s, 1H), 9.2 (d, J=5.1, 1H), 8.16 (d, J=5.1, 7.91 (m, 1H), 7.07 (d, J=8.4, 2H), 7.02 (d, J=8.4, 2H), 4.96 (t, J=7.2, 2H), 2.52-2.64 (m, 7H), 2.00-2.06 (m, 2H), 1.60-1.70 (m, 2H), 1.60-1.60 (m, 2H), 1.29-1.36 (m, 2H), 0.90 (t, J=7.2, 3H); $^{13}$CNMR, 145.62, 144.71, 142.37, 140.84, 139.73, 138.32, 128.66, 128.48, 127.78, 61.82, 35.54, 34.95, 34.05, 31.71, 27.93, 22.72, 19.07, 14.33.

Example 16

Synthesis of compound 1-[4-(4-butyl-phenyl)-butyl]-4-methyl-pyridinium bromide 1-(4-Bromo-butyl)-4-butyl-benzene (1 mmol) was added to a solution of 4-picoline (3 mmol) in acetonitrile, and the solution was refluxed for 24 hours. The acetonitrile was removed in a vacuum, and the resulting residue was partitioned between ether and water. The aqueous layer was washed extensively with ether until no picoline was left in the aqueous layer. The resulting aqueous solution of the product was extracted with chloroform. The chloroform was removed to afford the product (72%). $^1$HNMR (300 MHz, CDCl3, ppm), 9.22 (d, J=6.6, 2H), 7.79 (d, J=6.6, 2H), 7.05 (d, J=8.4, 2H), 7.02 (d, J=8.4, 2H), 4.90 (t, J=7.5, 3H), 2.51-2.63 (m, 7H), 1.96-2.06 (m, 2H), 1.58-1.68 (m, 2H), 1.51-1.61 (m, 2H), 1.31-1.37 (m, 2H), 0.89 (t, J=7.2, 3H); $^{13}$CNMR, 158.91, 144.31, 140.83, 138.30, 128.92, 128.66, 128.45, 61.26, 35.54, 34.95, 34.04, 31.61, 27.95, 22.73, 22.57, 14.33.

Example 17

Synthesis of 2-[4-(4-butyl-phenyl)-butyl]-5,6,7,8-tetrahydro-isoquinolinium bromide

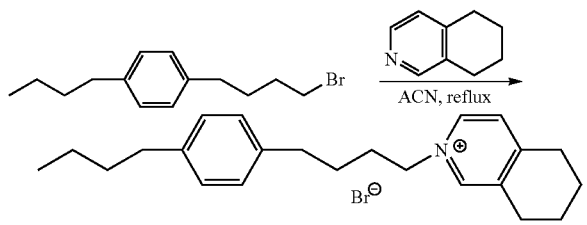

1-(4-Bromo-butyl)-4-butyl-benzene (1 mmol) was added to a solution of tetrahydroisoquinoline (2 mmol) in acetonitrile, and the solution was refluxed for 24 hours. The acetonitrile was removed in vacuum, and the resulting residue was partitioned between ether and water. The aqueous layer was washed extensively with ether until no tetrahydroisoquinoline was left in the aqueous layer. The resulting aqueous solution of the product was extracted with chloroform. The chloroform was removed to afford the product (72%). $^1$HNMR (300 MHz, CDCl3, ppm), 9.12 (s, 1H), 8.85 (d, J=6.0, 1H), 7.61 (d, J=6.0, 1H), 7.02-7.08 (m, 4H), 4.83 (t, 7.5, 3H), 2.92-2.94 (m, 4H), 2.61 (t, J=7.5, 2H), 2.54 (t, J=7.5, 2H), 1.90-2.04 (m, 2H), 1.80-1.90 (m, 4H), 1.62-1.69 (m, 2H), 1.53-1.62 (m, 2H), 1.29-1.37 (m, 2H), 0.90 (t, J=7.2, 3H). $^{13}$CNMR, 157.94, 144.18, 140.82, 140.64. 138.96, 138.37, 128.65, 128.48, 127.99, 61.16, 35.54, 34.99, 34.05, 31.56, 29.92, 27.98, 26.69, 22.74, 21.37, 14.33.

Example 18

Synthesis of 1-[4-(4-butyl-phenyl)-butyl]-3-(3-hydroxy-propyl)-pyridinium bromide

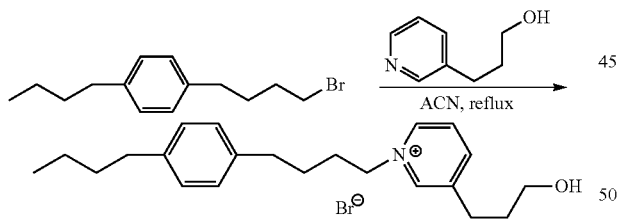

1-(4-Bromo-butyl)-4-butyl-benzene (1 mmol) was added to a solution of hydroxypropanylpyridine (2 mmol) in acetonitrile, and the solution was refluxed for 24 hours. The acetonitrile was removed in a vacuum, and the resulting residue was partitioned between ether and water. The aqueous layer was washed extensively with ether until no hydroxypropanylpyridine was left in the aqueous layer. The resulting aqueous solution of the product was extracted with chloroform. The chloroform was removed to afford the product (65%). $^1$HNMR (300 MHz, CDCl3, ppm), 9.41 (s, 1H), 8.85 (d, J=6.3, 1H), 8.26 (d, J=8.1, 1H), 7.89 (dd, J=6.3, J=8.1, 1H), 7.02-7.07 (m, 4H), 4.90 (t, J=7.5, 2H), 3.59 (t, J=5.4, 2H), 3.00 (t, J=6.9, 2H), 2.62 (t, J=7.2, 2H), 2.55 (t, J=7.8, 2H), 1.95-2.05 (m, 4H), 1.57-1.69 (m, 2H), 1.50-1.60 (m, 2H), 1.29-1.37 (m, 2H), 0.90 (t, J=7.2, 3H).

Example 19

Synthesis of compound 1-[4-(4-butyl-phenyl)-butyl]-2,4-dimethyl-pyridinium bromide

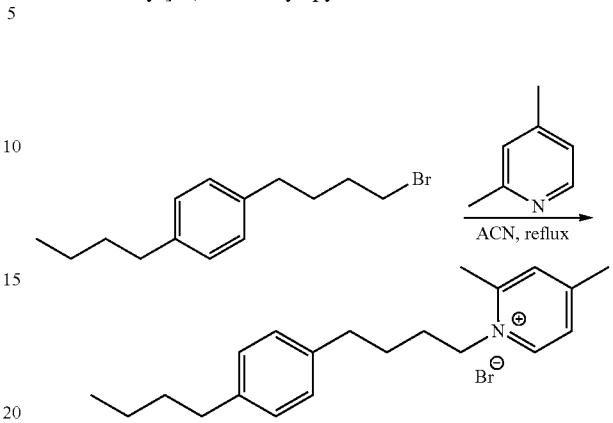

1-(4-Bromo-butyl)-4-butyl-benzene (1 mmol) was added to a solution of 2,4-lutidine (3 mmol) in acetonitrile, and the solution was refluxed for 24 hours. The acetonitrile was removed in a vacuum, and the resulting residue was partitioned between ether and water. The aqueous layer was washed extensively with ether until no lutidine left in the aqueous layer. The resulting aqueous solution of the product was extracted with chloroform. The chloroform was removed to afford the product (79%). $^1$HNMR (300 MHz, CDCl3, ppm), 9.51 (d, J=6.2, 1H), 7.67 (d, J=6.2, 1H), 7.54 (s, 1H), 7.05-7.07 (m, 4H), 4.83 (t, J=7.2, 2H), 2.77 (s, 3H), 2.64 (t, J=7.2, 2H), 2.52-2.58 (m, 5H), 1.87-1.92 (m, 2H), 1.76-1.82 (m, 2H), 1.50-1.58 (m, 2H), 1.29-1.37 (m, 2H), 0.91 (t, J=7.8, 3H).

Example 20

Synthesis of 1-[4-(4-butyl-phenyl)-butyl]-3,4-dimethyl-pyridinium bromide

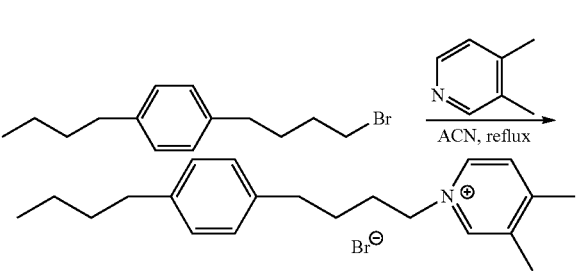

1-(4-Bromo-butyl)-4-butyl-benzene (1 mmol) was added to a solution of 3,4-lutidine (3 mmol) in acetonitrile, and the solution was refluxed for 24 hours. The acetonitrile was removed in a vacuum, and the resulting residue was partitioned between ether and water. The aqueous layer was washed extensively with ether until no lutidine left in the aqueous layer. The resulting aqueous solution of the product was extracted with chloroform. The chloroform was removed to afford the product (79%). 1HNMR (300 MHz, CDCl3, ppm), 9.20 (s, 1H), 9.03 (d, J=6.3, 1H), 7.72 (d, J=6.3, 1H), 7.00-7.07 (m, 4H), 4.87 (t, J=7.5, 2H), 2.60 (t, J=7.8, 2H), 2.54 (t, J=7.8, 2H), 2.49 (s, 3H), 2.46 (s, 3H), 1.99-2.04 (m, 2H), 1.50-1.66 (m, 4H), 1.28-1.36 (m, 2H), 0.90 (t, J=7.5, 3H). $^{13}$CNMR 157.60, 143.56, 141.92, 140.78, 138.40, 128.63, 128.57, 128.47, 61.00, 35.54, 34.98, 34.04, 31.59, 27.96, 22.73, 20.66, 17.36, 14.31.

Example 21

Synthesis of 1-[4-(4-butyl-phenyl)-butyl]-3,5-dimethyl-pyridinium bromide

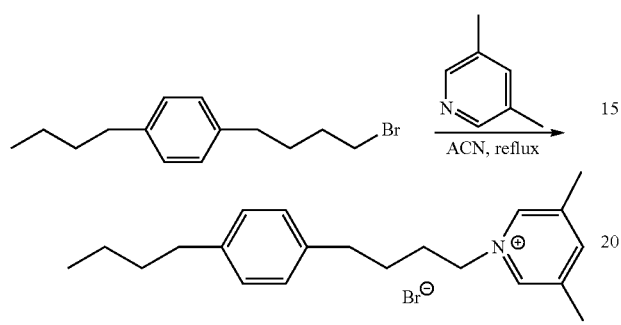

1-(4-Bromo-butyl)-4-butyl-benzene (1 mmol) was added to a solution of 3,5-lutidine (3 mmol) in acetonitrile, and the solution was refluxed for 24 hours. The acetonitrile was removed in a vacuum, and the resulting residue was partitioned between ether and water. The aqueous layer was washed extensively with ether until no lutidine was left in the aqueous layer. The resulting aqueous solution of the product was extracted with chloroform. The chloroform was removed to afford the product (81%). 1HNMR (300 MHz, CDCl3, ppm), 9.11 (s, 2H), 7.92 (s, 1H), 7.00-7.06 (m, 4H), 4.88 (t, J=7.5, 2H), 2.51-2.62 (m, 7H), 1.99-2.05 (m, 2H), 1.49-1.66 (m, 4H), 1.28-1.35 (m, 2H), 0.89 (t, J=7.2, 3H). $^{13}$CNMR, 146.17, 141.96, 140.81, 138.91, 138.40, 128.63, 128.48, 61.60, 35.54, 34.98, 34.05, 31.68, 27.95, 22.72, 18.88, 14.31.

Example 22

Synthesis of compound 1-[4-(4-butyl-phenyl)-but-3-ynyl]-3-methyl-pyridinium bromide

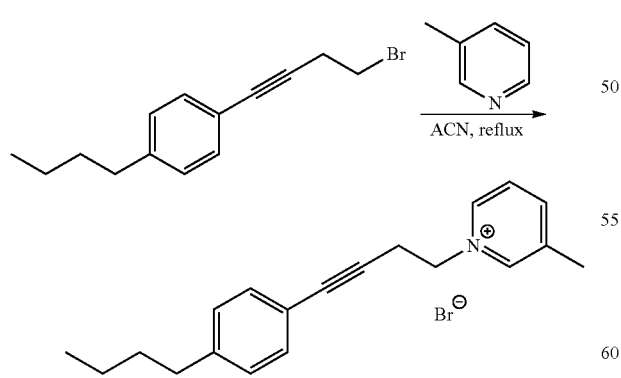

1-(4-Bromo-but-1-ynyl)-4-butyl-benzene (1 mmol) was added to a solution of 3-picoline (3 mmol) in acetonitrile, and the solution was refluxed for 24 hours. The acetonitrile was removed in a vacuum, and the resulting residue was partitioned between ether and water. The aqueous layer was washed extensively with ether until no picoline was left in the aqueous layer. The resulting aqueous solution of the product was extracted with chloroform. The chloroform was removed to afford the product (77%). $^1$HNMR R (300 MHz, CDCl3, ppm), 9.48 (s, 1H), 9.33 (d, J=6.6, 1H), 8.24 (d, J=7.2, 1H), 7.93 (dd, J=6.6, J=7.2, 1H), 7.16 (d, J=8.2, 2H), 7.06 (d, J=8.2, 2H), 5.21 (t, J=6.0, 2H), 3.26 (t, J=6.0, 2H), 2.59 (s, 3H), 2.56 (t, 2H), 1.49-1.59 (m 2H), 1.25-1.37 (m, 2H), 0.9 (t, J=7.2, 3H); $^{13}$CNMR, 145.70, 144.78, 143.64, 142.26, 138.98, 131.15, 128.32, 126.94, 118.92, 85.84, 82.45, 59.90, 35.45, 33.28, 22.81. 22.24, 18.71, 13.89.

Example 23

Synthesis of compound 1-[4-(4-butyl-phenyl)-but-3-ynyl]-4-methyl-pyridinium bromide

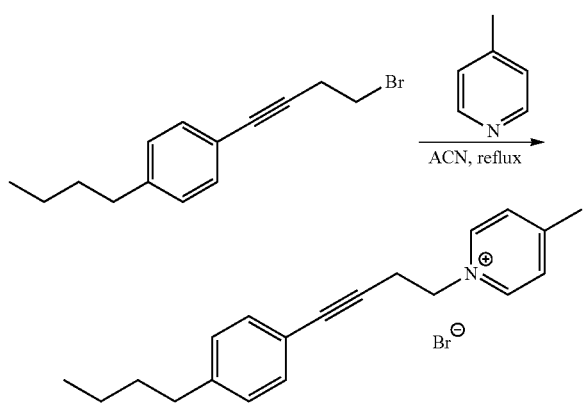

1-(4-Bromo-but-1-ynyl)-4-butyl-benzene (1 mmol) was added to a solution of 4-picoline (3 mmol) in acetonitrile, and the solution was refluxed for 24 hours. The acetonitrile was removed in vacuum, and the resulting residue was partitioned between ether and water. The aqueous layer was washed extensively with ether until no picoline was left in the aqueous layer. The resulting aqueous solution of the product was extracted with chloroform. The chloroform was removed to afford the product (67%). $^1$HNMR (300 MHz, CDCl3, ppm), 9.40 (d, J=6.9, 1H), 7.80 (d, 1H), 7.17 (d, J=7.8, 2H), 7.06 (d, J=7.8, 2H), 5.2 (t, 2H), 3.23 (t, 2H), 2.65 (s, 3H), 2.56 (t, J=7.8, 2H), 1.49-1.57 (m, 2H), 1.27-1.35 (m, 2H), 0.90 (t, J=7.5, 3H).

Example 24

Synthesis of 1-[4-(4-butyl-phenyl)-but-3-ynyl]-3-ethyl-pyridinium bromide

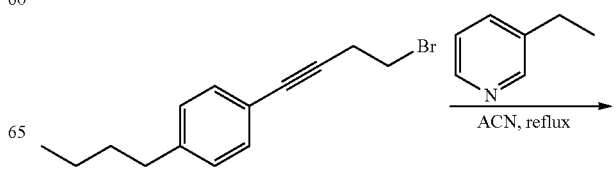

-continued

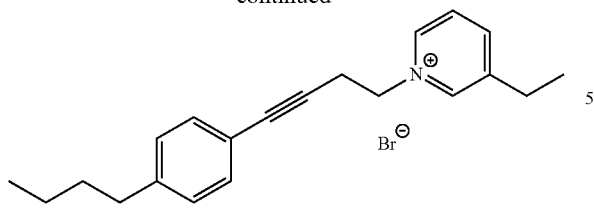

1-(4-Bromo-but-1-ynyl)-4-butyl-benzene (1 mmol) was added to a solution of 3-ethylpyridine (3 mmol) in acetonitrile, and the solution was refluxed for 24 hours. The acetonitrile was removed in vacuum, and the resulting residue was partitioned between ether and water. The aqueous layer was washed extensively with ether until no ethylpyridine was left in the aqueous layer. The resulting aqueous solution of the product was extracted with chloroform. The chloroform was removed to afford the product (67%). 1HNMR (300 MHz, CDCl3, ppm), 9.43 (d, J=6.0, 1H), 9.41 (s, 1H), 8.25 (d, J=8.1, 1H), 7.96 (dd, J=6.0, J=8.1, 1H), 7.15 (d, J=8.1, 2H), 7.06, d, J=8.1, 2H), 5.26 (t, J=6.0, 2H), 3.26 (t, J=6.0, 2H), 2.90 (q, J=7.5, 2H), 2.56 (t, J=8.1, 2H), 1.49-1.59 (m, 2H), 1.27-1.37 (m, 5H), 0.90 (t, J=7.2, 3H); $^{13}$CNMR, 144.65, 144.46, 144.14, 143.65, 142.45, 131.14, 128.30, 127.12, 118.87, 85.88, 82.45, 59.99, 35.45, 33.27, 26.01, 22.85, 22.21, 14.26, 13.88.

Example 25

Synthesis of 2-[4-(4-butyl-phenyl)-but-3-ynyl]-5,6,7,8-tetrahydro-isoquinolinium bromide

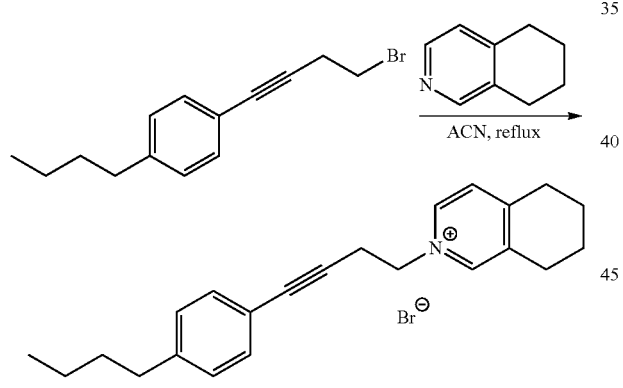

1-(4-Bromo-but-1-ynyl)-4-butyl-benzene (1 mmol) was added to a solution of tetrahydroisoquinoline (2 mmol) in acetonitrile, and the solution was refluxed for 24 hours. The acetonitrile was removed in a vacuum, and the resulting residue was partitioned between ether and water. The aqueous layer was washed extensively with ether until no tetrahydroisoquinoline was left in the aqueous layer. The resulting aqueous solution of the product was extracted with chloroform. The chloroform was removed to afford the product (68%). 1HNMR (300 MHz, CDCl3, ppm), 9.30 (s, 1H), 9.04 (d, J=6.3, 2H), 7.62 (d, J=6.3, 1H), 7.18 (d, J=8.4, 2H), 7.06 (d, J=8.4, 2H), 5.10 (t, J=6.0, 3.21 (t, J=6.0, 2H), 2.94-2.96 (m, 2H), 2.56 (t, J=8.1, 2H), 1.81-1.87 (m, 2H), 1.49-1.56 (m, 2H), 1.27-1.34 (m, 2H), 0.89 (t, J=7.2, 3H); $^{13}$CNMR, 158.51, 144.59, 143.95, 140.93, 138.61, 131.55, 128.71, 127.57, 119.46, 85.97, 83.23, 59.58, 35.86, 33.69, 31.01, 26.70, 23.12, 22.63, 21.37, 14.28.

Example 26

Synthesis of 1-[4-(4-butyl-phenyl)-but-3-ynyl]-3,4-dimethyl-pyridinium bromide

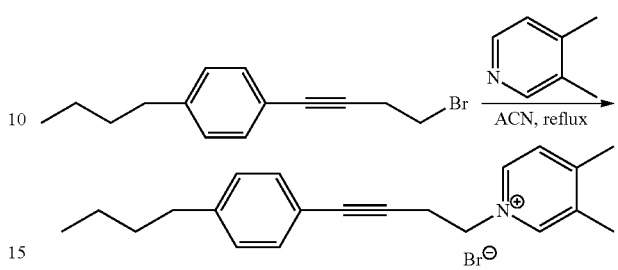

1-(4-Bromo-but-1-ynyl)-4-butyl-benzene (1 mmol) was added to a solution of 3-hydroxypropanylpyridine (2 mmol) in acetonitrile, and the solution was refluxed for 24 hours. The acetonitrile was removed in a vacuum, and the resulting residue was partitioned between ether and water. The aqueous layer was washed extensively with ether until no hydroxypropanylpyridine was left in the aqueous layer. The resulting aqueous solution of the product was extracted with chloroform. The chloroform was removed to afford the product (60%). 1HNMR (300 MHz, CDCl3, ppm), 9.39 (s, 1H), 9.13 (d, J=6.3, 1H), 7.70 (d, J=6.3, 1H), 7.17 (d, J=8.1, 2H), 7.07 (d, J=8.1, 2H), 5.13 (t, J=6.0, 2H), 3.23 (t, J=6.0, 2H), 2.57 (t, J=7.8, 2H), 2.53 (s, 3H), 2.48 (s, 3H), 1.50-1.58 (m, 2H), 1.28-1.37 (m, 2H), 0.90 (t, J=7.2, 3H); $^{13}$CNMR, 158.19, 143.98, 138.11, 131.53, 128.69, 128.05, 119.45, 83.11, 59.60, 35.84, 33.64, 23.12, 22.62, 20.77, 17.35, 14.23.

Example 27

Synthesis of 1-[4-(4-butyl-phenyl)-but-3-ynyl]-3,5-dimethyl-pyridinium bromide

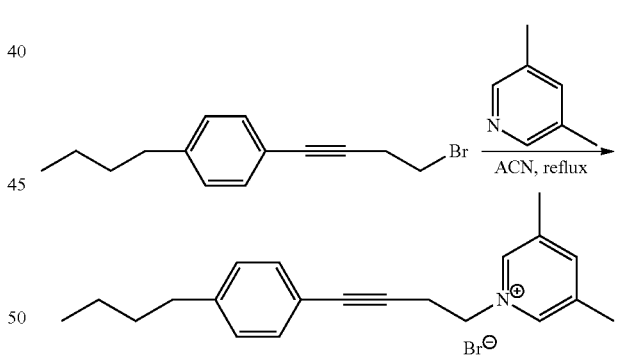

1-(4-Bromo-but-1-ynyl)-4-butyl-benzene (1 mmol) was added to a solution of 3,5-lutidine (2 mmol) in acetonitrile, and the solution was refluxed for 24 hours. The acetonitrile was removed in a vacuum, and the resulting residue was partitioned between ether and water. The aqueous layer was washed extensively with ether until no lutidine was left in the aqueous layer. The resulting aqueous solution of the product was extracted with chloroform. The chloroform was removed to afford the product (80%). 1HNMR (300 MHz, CDCl3, ppm), 9.39 (s, 1H), 9.13 (d, J=6.3, 1H), 7.70 (d, J=6.3, 1H), 7.17 (d, J=8.1, 2H), 7.07 (d, J=8.1, 2H), 5.13 (t, J=6.0, 2H), 3.23 (t, J=6.0, 2H), 2.57 (t, J=7.8, 2H), 2.53 (s, 3H), 2.48 (s, 3H), 1.50-1.58 (m, 2H), 1.28-1.37 (m, 2H), 0.90 (t, J=7.2, 3H); $^{13}$CNMR, 158.19, 143.98, 138.11, 131.53, 128.69, 128.05, 119.45, 83.11, 59.60, 35.84, 33.64, 23.12, 22.62, 20.77, 17.35, 14.23.

Example 28

Synthesis of 1-[4-(4-butyl-phenyl)-but-3-ynyl]-3-(3-hydroxy-propyl)-pyridinium bromide

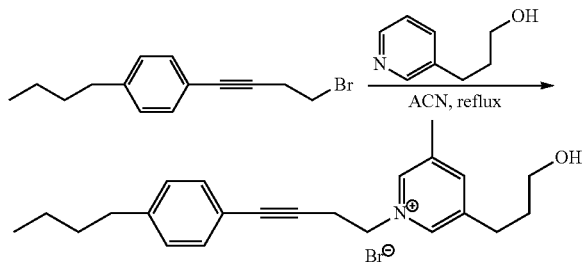

1-(4-Bromo-but-1-ynyl)-4-butyl-benzene (1 mmol) was added to a solution of 3-hydroxypropanylpyridine (2 mmol) in acetonitrile, and the solution was refluxed for 24 hours. The acetonitrile was removed in vacuum, and the resulting residue was partitioned between ether and water. The aqueous layer was washed extensively with ether until no hydroxypropanylpyridine was left in the aqueous layer. The resulting aqueous solution of the product was extracted with chloroform. The chloroform was removed to afford the product (60%). 1HNMR (300 MHz, CDCl3, ppm), 9.46 (s, 1H), 9.04 (d, J=6.0, 1H), 8.33 (d, J=8.1, 1H), 7.92 (dd, J=6.0, J=8.1, 1H), 7.16 (d, J=8.4, 2H), 7.04 (d, J=8.1, 2H), 5.12 (t, J=6.6, 2H), 3.57 (t, 6.0, 2H), 3.22 (t, J=6.0, 2H), 2.98 (t, J=7.2, 2H), 2.54 (t, J=7.5, 3H), 1.94 (p, 6.0, 2H), 1.47-1.57 (m, 2H), 1.26-1.34 (m, 2H), 0.89 (t, J=7.5, 3H); $^{13}$CNMR, 145.54, 144.99, 143.62, 141.83, 131.20, 128.32, 126.94, 118.95, 85.65, 82.43, 59.92, 59.78, 58.26, 35.44, 33.28, 32.33, 29.24, 22.68, 22.23, 18.39, 13.88.

Example 29

Synthesis of compound 3-methyl-1-(13-pyridin-3-yl-tridecyl)-pyridinium bromide

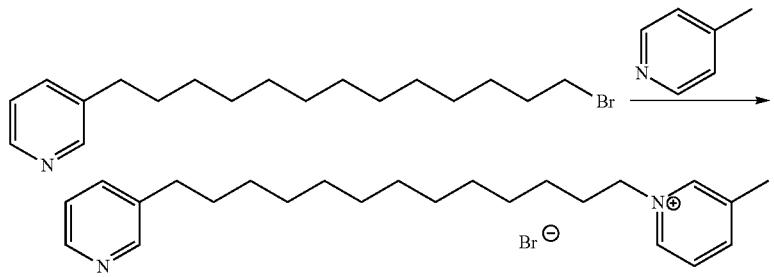

3-(13-Bromo-tridecyl)-pyridine (1 mmol) was added to 3-picoline (5 ml), and the mixture was heated at 50 C overnight. The excess picoline was removed in vacuum, and the resulting residue was partitioned between water and ether. The aqueous layer was washed extensively with ether until no picoline left in the aqueous layer, and then the aqueous layer was extracted with chloroform. The chloroform was removed to afford the product (65%). $^1$HNMR (300 MHz, CDCl3, ppm), 9.36 (s, 1H), 9.22 (d, J=5.4, 1H), 8.44 (br, 2H), 8.21 (d, J=7.5, 1H), 7.97 (m, 1H), 7.54 (d, 7.2, 1H), 7.24-7.24 m, 1H), 4.96 (t, J=7.2, 2H), 2.58-2.65 M, 5H), 2.00-2.07 (m, 4H), 1.58-1.60 (m, 2H), 1.20-1.36 (m, 16H); $^{13}$CNMR, 148.76, 146.10, 145.58, 144.77, 142.38, 139.83, 137.29, 127.80, 123.98, 62.28, 58.71, 33.31, 32.36, 31.32, 29.80, 29.74, 29.64, 29.38, 29.35, 26.45, 19.15, 18.81.

Example 30

Synthesis of compound 3,4-dimethyl-1-(13-pyridin-3-yl-tridecyl)-pyridinium bromide

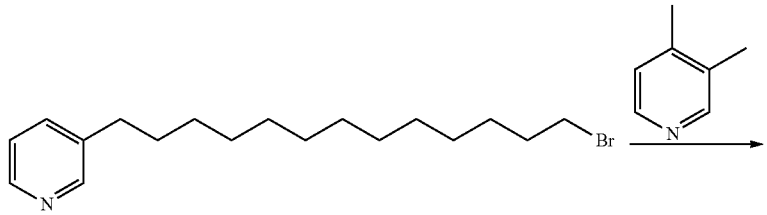

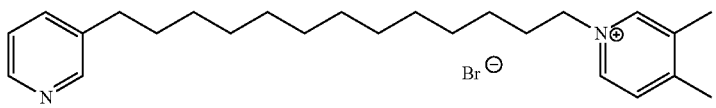

3-(13-Bromo-tridecyl)-pyridine (1 mmol) was added to 3,4-lutidine (5 ml), and the mixture was heated at 50 C overnight. The excess picoline was removed in a vacuum, and the resulting residue was partitioned between water and ether. The aqueous layer was washed extensively with ether until no 3,4-lutidine was left in the aqueous layer, and then the aqueous layer was extracted with chloroform. The chloroform was removed to afford the product (60%). $^1$HNMR (300 MHz, CDCl3, ppm), 9.23 (s, 1H), 9.04 (d, J=6.3, 1H), 8.40 (br, 2H), 7.79 (d, J=6.0, 1H), 7.48 (d, 8.1, 1H), 7.18-7.20 (m, 1H), 4.83 (t, J=7.5, 2H), 2.58 (t, J=7.5, 2H), 2.52 (s, 3H), 2.49 (s, 3H), 2.21 (br, 1H), 1.82-2.02 (m, 2H), 1.54-1.62 (m, 2H), 1.15-1.35 (br, 12H). $^{13}$CNMR, 157.61, 149.68, 146.92, 143.35, 141.91, 138.45, 138.33, 136.32, 128.65, 123.57, 61.37, 33.31, 32.19, 31.41, 29.85, 29.80, 29.68, 29.41, 26.45, 20.69, 17.40.

Example 31

Synthesis of compound 3,5-dimethyl-1-(13-pyridin-3-yl-tridecyl)-pyridinium bromide until no 3,5-lutidine was left in the aqueous layer, and then the aqueous layer was extracted with chloroform. The chloroform was removed to afford the product (62%). $^1$HNMR (300 MHz, CDCl3, ppm), 9.10 (s, 2H), 8.45 (br, 2H), 7.96 (s, 1H), 7.57 (d, J=7.5, 1H), 7.24-7.27 (m, 1H), 4.89 (t, J=7.5, 2H), 2.59-2.54 (m, 8H), 1.99-2.04 (m, 2H), 1.57-1.62 (m, 2H), 1.21-1.38 (m, 18H), $^{13}$CNMR, 148.07, 146.11, 145.45, 141.94, 139.01, 137.96, 124.16, 62.13, 58.74, 33.29, 32.34, 31.26, 29.76, 29.73, 29.62, 29.39, 29.30, 26.49, 18.98, 18.82.

Example 32

Synthesis of compound 2-(13-pyridin-3-yl-tridecyl)-5,6,7,8-tetrahydro-isoquinolinium bromide

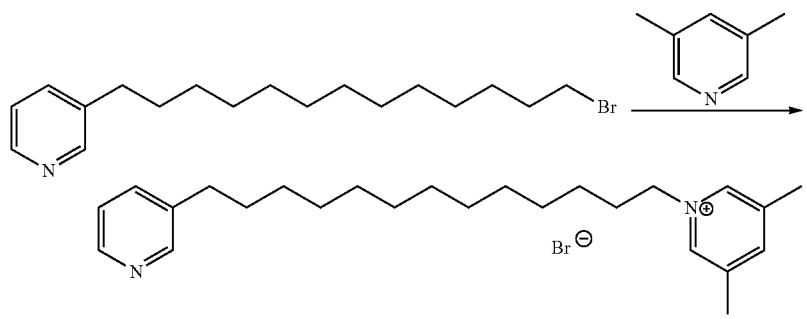

3-(13-Bromo-tridecyl)-pyridine (1 mmol) was added to 3,5-lutidine (5 ml), and the mixture was heated at 50 C overnight. The excess picoline was removed in a vacuum, and the resulting residue was partitioned between water and ether. The aqueous layer was washed extensively with ether

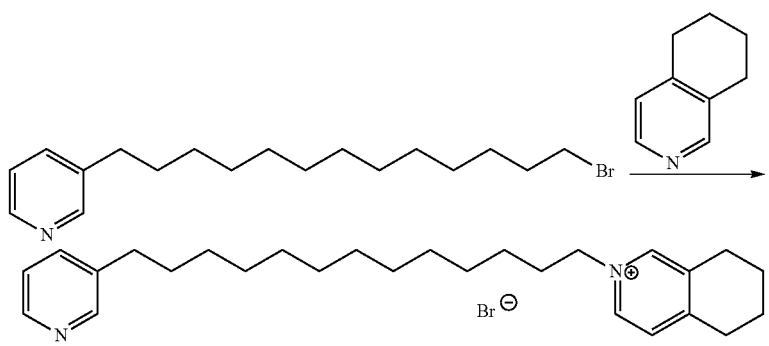

3-(13-Bromo-tridecyl)-pyridine (1 mmol) was added to 5,6,7,8-tetrahydro-isoquinoline (5 ml), and the mixture was heated at 50 C overnight. The resulting residue was treated with ether, and the ether was decanted after deposition for 30'. The residue was partitioned between water and ether. The aqueous layer was washed extensively with ether, and then the aqueous layer was extracted with chloroform. The chloroform was removed to afford the product (62%). ¹HNMR (300 MHz, CDCl3, ppm), 9.22 (s, 1H), 8.90 (d, J=6.3, 1H), 8.44 (br, 2H), 7.67 (d, J=6.3, 1H), 7.55 (d, 8.1, 7.24-7.28 (m, 1H), 4.83 (t, J=7.2, 2.98-3.01 (m, 4H), 2.60 (t, J=7.8, 2H), 1.94-2.02 (m, 2H), 1.87-1.90 (m, 4H), 1.56-1.60 (m, 2H), 1.19-1.35 (br, 20H); ¹³CNMR, 157.87, 148.79, 146.13, 144.20, 140.68, 138.95, 138.80, 137.26, 128.08, 123.92, 61.40, 58.62, 33.30, 32.20, 31.34, 29.94, 29.82, 29.77, 29.67, 29.42, 29.36, 26.71, 26.46, 21.40, 18.81.

Example 33

Synthesis of compound 5-(1,1'-biphenyl-4-yl)-pent-4-yn-1-ol

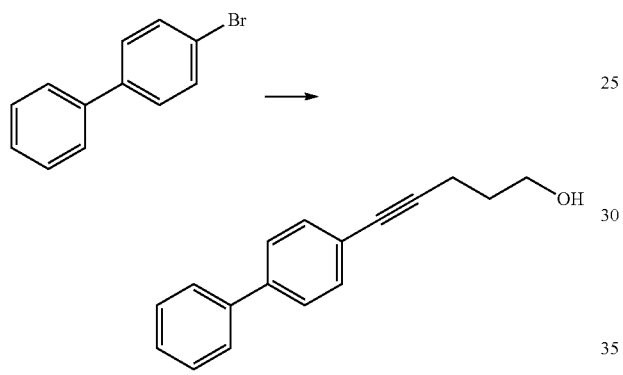

4-Bromobiphenyl (10.28 g, 44.10 mmol), 4-pentyn-1-ol (4.45 g, 52.92 mmol), and bis(triphenylphosphine)palladium (II) dichloride (310 mg, 0.44 mmol) were stirred in triethylamine (100 mL) under nitrogen for 5 min. Copper(I) iodide (42 mg, 0.22 mmol) was added, and the mixture was stirred for 4 hrs at 65° C. The mixture was cooled to room temperature and filtered through a celite pad, rinsed with ethylacetate. The combined filtrate was evaporated to dryness under reduced pressure. The resulting residue was purified by column chromatography (hexanes:ethylacetate 3:2) to afford 7.78 g of the title compound. Yield: 75%. ¹H NMR (300 MHz, CDCl₃) δ 1.88 (m, 2H), 2.57 (t, J=6.9 Hz, 2H), 3.84 (t, J=6.0 Hz, 2H), 7.32-7.60 (m, 9H) ppm; ¹³C NMR (75 MHz, CDCl₃) δ 16.4, 31.7, 62.1, 81.2, 90.2, 122.8, 127.0, 127.1, 127.6, 128.9, 132.0, 140.1 ppm.

Example 34

Synthesis of compound 4-(5-bromo-pent-1-ynl)-1,1'-biphenyl

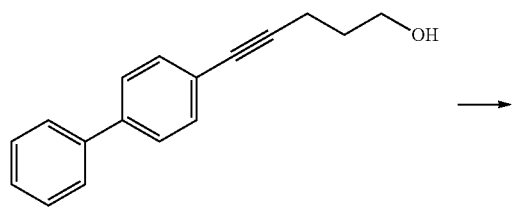

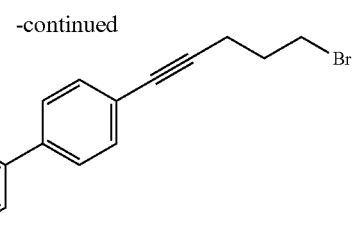

5-(1,1'-biphenyl-4-yl)-4-pentyn-1-ol (3.40 g, 14.39 mmol) and carbon tetrabromide (6.21 g, 18.71 mmol) were dissolved in dry methylene chloride (20 mL) and cooled to 0° C. Triphenyl phosphine (5.15 g, 19.65 mmol) in methylene chloride (10 mL) was added dropwise, and the mixture was stirred for 1 h at 0° C. The mixture was poured into hexanes (100 mL), and then filtered through a short silica gel column, washed with ethylacetate/hexanes (1/4). The combined organic solvents were evaporated to dryness under reduced pressure. The resulting residue was purified by column chromatography (hexanes:ethylacetate 30:1) to afford 4.20 g of the title compound. Yield: 97%. ¹H NMR (300 MHz, CDCl₃) δ 2.15 (m, 2H), 2.63 (t, J=6.9 Hz, 2H), 3.60 (t, J=6.3 Hz, 2H), 7.32-7.60 (m, 9H) ppm; ¹³C NMR (75 MHz, CDCl₃) δ 18.5, 31.8, 32.8, 81.7, 88.8, 122.6, 127.0, 127.1, 127.6, 128.9, 132.1, 140.5, 140.6 ppm.

Example 35

Synthesis of compound 1-[5-(1,1'-biphenyl-4-yl)-pent-4-ynyl]-2-methyl-pyridinium bromide

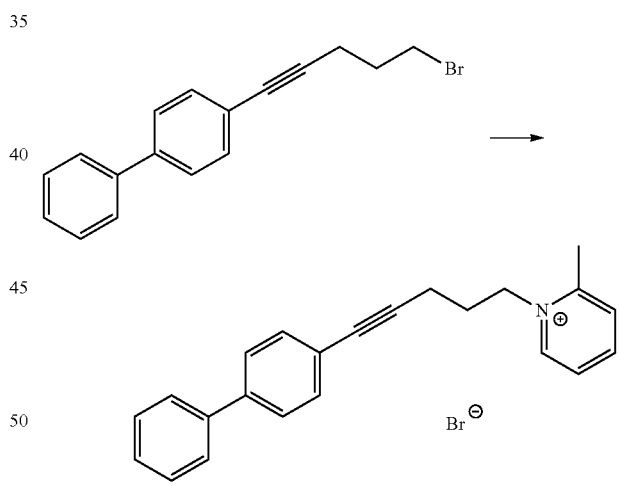

A mixture of 4-(5-bromo-1-pentynl)-1,1'-biphenyl (357 mg, 1.19 mmol) and 2-picoline (1 mL) was heated at 60-70° C. for 12 hrs. The resulted mixture was washed with diethyl ether and then dissolved in water (15 mL). The aqueous solution was extracted with diethyl ether (30 mL×3). Water was removed by lyophilization to afford 393 mg of the title compound. Yield: 84%. ¹H NMR (300 MHz, CDCl₃) δ 2.31 (m, 2H), 2.75 (t, J=6.3 Hz, 2H), 3.04 (s, 3H), 5.14 (t, J=7.8 Hz, 2H), 7.30-7.59 (m, 9H), 7.94-8.01 (m, 2H), 8.38 (t, J=7.8 Hz, 1H), 9.82 (d, J=6.0 Hz, 1H) ppm; ¹³C NMR (75 MHz, CDCl₃) δ 16.9, 21.1, 29.7, 57.2, 82.4, 88.1, 121.8, 126.4, 127.0, 127.1, 127.7, 128.9, 130.3, 132.0, 140.1, 140.8, 145.3, 146.8, 154.6 ppm.

Example 36

Synthesis of compound 1-[5-(1,1'-biphenyl-4-yl)-pent-4-ynyl]-3-methyl-pyridinium bromide

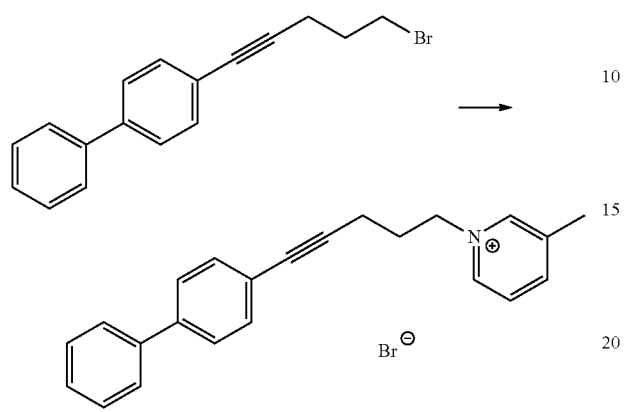

A mixture of 4-(5-bromo-1-pentynl)-1,1'-biphenyl (377 mg, 1.26 mmol) and 3-picoline (1 mL) was heated at 60-70° C. for 12 hrs. The resulting mixture was washed with diethyl ether and then dissolved in water (15 mL). The aqueous solution was extracted with diethyl ether (30 mL×3). Water was removed by lyophilization to afford 433 mg of the title compound. Yield: 88%. $^1$H NMR (300 MHz, CDCl$_3$) δ 2.43 (m, 2H), 2.58 (s, 3H), 2.67 (t, J=6.6 Hz, 2H), 5.16 (t, J=6.9 Hz, 2H), 7.30-7.61 (m, 9H), 7.98 (dd, J=8.1, 6.0 Hz, 1H), 8.16 (d, J=8.1 Hz, 1H), 9.37 (d, J=6.0 Hz, 1H), 9.50 (s, 1H) ppm; $^{13}$C NMR (75 MHz, CDCl$_3$) δ 16.8, 19.0, 30.5, 60.9, 82.4, 88.0, 121.9, 126.9, 127.7, 127.8, 128.9, 132.0, 139.7, 140.1, 140.7, 142.5, 144.8, 145.8 ppm.

Example 37

Synthesis of compound 1-[5-(1,1'-biphenyl-4-yl)-pent-4-ynyl]-4-methyl-pyridinium bromide

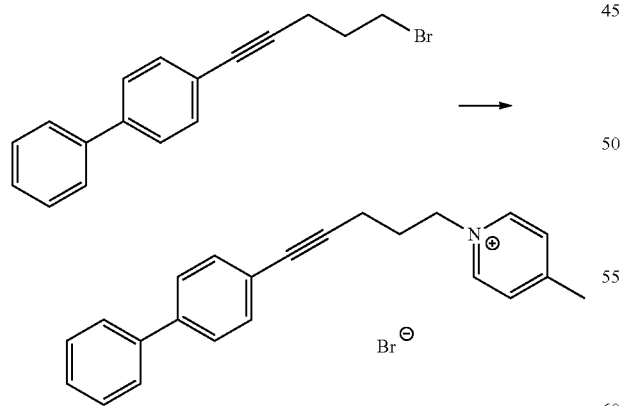

A mixture of 4-(5-bromo-1-pentynl)-1,1'-biphenyl (360 mg, 1.20 mmol) and 4-picoline (1 mL) was heated at 60-70° C. for 12 hrs. The resulted mixture was washed with diethyl ether and then dissolved in water (15 mL). The aqueous solution was extracted with diethyl ether (30 mL×3). Water was removed by lyophilization to afford 435 mg of the title compound. Yield: 92%. $^1$H NMR (300 MHz, CDCl$_3$) δ 2.40 (m, 2H), 2.49 (s, 3H), 2.67 (t, J=6.6 Hz, 2H), 5.16 (t, J=6.9 Hz, 2H), 7.30-7.59 (m, 9H), 7.80 (d, J=6.3 Hz, 2H), 9.43 (d, J=6.3 Hz, 2H) ppm; $^{13}$C NMR (75 MHz, CDCl$_3$) δ 16.8, 22.4, 30.3, 60.3, 82.3, 88.0, 121.9, 126.9, 127.0, 127.8, 128.8, 129.0, 132.0, 140.1, 140.7, 144.5, 159.2 ppm.

Example 38

Synthesis of compound 1-[5-(1,1'-biphenyl-4-yl)-pent-4-ynyl]-2,4-dimethyl-pyridinium bromide

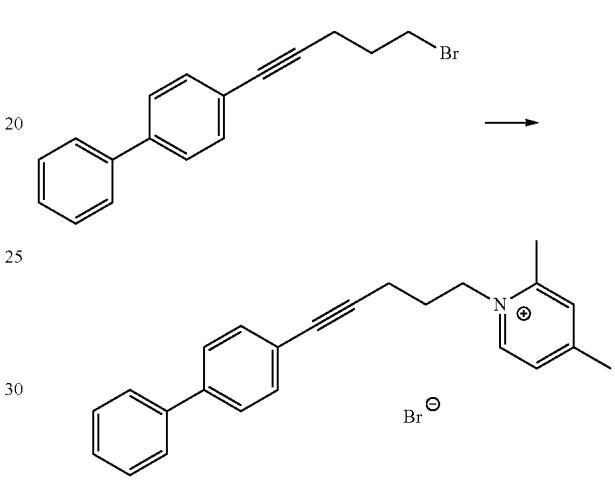

A mixture of 4-(5-bromo-1-pentynl)-1,1'-biphenyl (328 mg, 1.10 mmol) and 2,4-lutidine (1 mL) was heated at 60-70° C. for 12 hrs. The resulting mixture was washed with diethyl ether, and then dissolved in water (15 mL). The aqueous solution was extracted with diethyl ether (30 mL×3). Water was removed by lyophilization to afford 360 mg of the title compound. Yield: 81%. $^1$H NMR (300 MHz, CDCl$_3$) δ 2.29 (m, 2H), 2.51 (s, 3H), 2.73 (t, J=6.3 Hz, 2H), 2.96 (s, 3H), 5.04 (t, J=7.5 Hz, 2H), 7.30-7.60 (m, 9H), 7.70 (s, 2H), 9.56 (d, J=7.2 Hz, 1H) ppm; $^{13}$C NMR (75 MHz, CDCl$_3$) δ 16.8, 20.7, 22.1, 29.4, 56.4, 82.2, 88.1, 121.8, 126.9, 127.0, 127.7, 128.9, 130.5, 131.9, 140.0, 140.7, 145.8, 153.3, 158.7 ppm.

Example 39

Synthesis of compound 1-[5-(1,1'-biphenyl-4-yl)-pent-4-ynyl]-3,4-dimethyl-pyridinium bromide

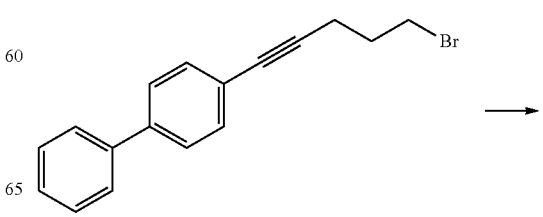

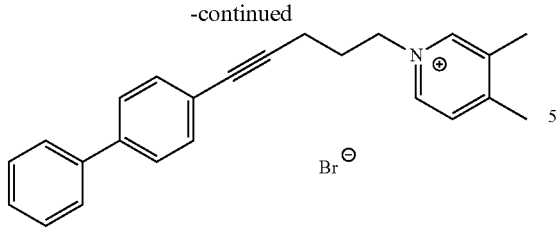

A mixture of 4-(5-bromo-1-pentynl)-1,1'-biphenyl (327 mg, 1.09 mmol) and 3,4-lutidine (1 mL) was heated at 60-70° C. for 12 hrs. The resulted mixture was washed with diethyl ether and then dissolved in water (15 mL). The aqueous solution was extracted with diethyl ether (30 mL×3). Water was removed by lyophilization to afford 380 mg of the title compound. Yield: 86%. $^1$H NMR (300 MHz, CDCl$_3$) δ 2.36 (s, 3H), 2.43 (s, 3H), 2.55 (m, 2H), 2.69 (t, J=6.6 Hz, 2H), 5.10 (t, J=6.6 Hz, 2H), 7.28-7.59 (m, 9H), 7.77 (d, J=6.0 Hz, 1H), 9.22 (d, J=6.0 Hz, 1H), 9.38 (s, 1H) ppm; $^{13}$C NMR (75 MHz, CDCl$_3$) δ 16.8, 17.2, 20.4, 30.2, 60.1, 82.0, 88.2, 122.0, 126.9, 127.7, 128.5, 128.9, 131.9, 138.2, 140.0, 140.6, 142.1, 143.7, 157.9 ppm.

Example 40

Synthesis of compound 1-[5-(1,1'-biphenyl-4-yl)-pent-4-ynyl]-3,5-dimethyl-pyridinium bromide

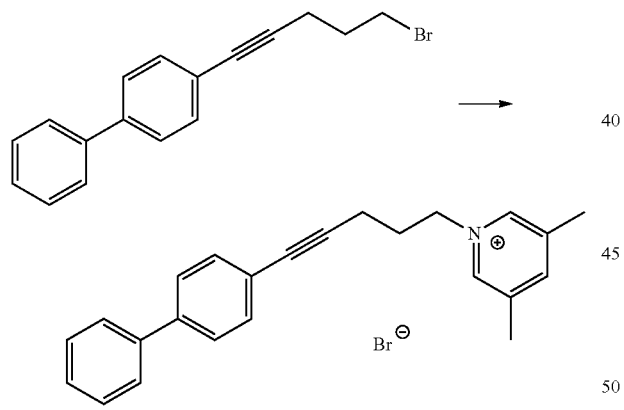

A mixture of 4-(5-bromo-1-pentynl)-1,1'-biphenyl (360 mg, 1.20 mmol) and 3,5-lutidine (1 mL) was heated at 60-70° C. for 12 hrs. The resulted mixture was washed with diethyl ether and then dissolved in water (15 mL). The aqueous solution was extracted with diethyl ether (30 mL×3). Water was removed by lyophilization to afford 439 mg of the title compound. Yield: 90%. $^1$H NMR (300 MHz, CDCl$_3$) δ 2.43 (m, 2H), 2.54 (s, 6H), 2.67 (t, J=6.6 Hz, 2H), 5.10 (t, J=6.9 Hz, 2H), 7.30-7.60 (m, 9H), 7.90 (s, 1H), 9.24 (s, 2H) ppm; $^{13}$C NMR (75 MHz, CDCl$_3$) δ 16.8, 18.8, 30.4, 60.7, 82.3, 88.1, 122.0, 127.0, 127.8, 129.0, 132.0, 138.9, 140.1, 140.8, 142.1, 146.4 ppm.

Example 41

Synthesis of compound 1-[5-(1,1'-biphenyl-4-yl)-pent-4-ynyl]-quinolinium bromide

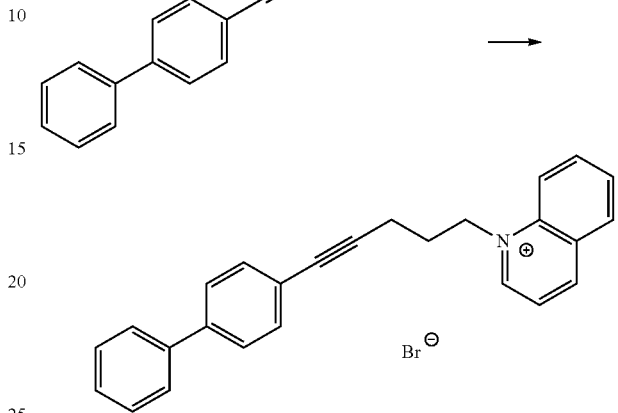

A mixture of 4-(5-bromo-1-pentynl)-1,1'-biphenyl (329 mg, 1.10 mmol) and quinoline (1 mL) was heated at 60-70° C. for 12 hrs. The resulted mixture was washed with diethyl ether and then dissolved in water (30 mL). The aqueous solution was extracted with ethyl acetate (30 mL×3). Water was removed by lyophilization to afford 328 mg of the title compound. Yield: 70%. $^1$H NMR (300 MHz, CDCl$_3$) δ 2.49 (m, 2H), 2.84 (t, J=6.3 Hz, 2H), 5.67 (t, J=7.2 Hz, 2H), 7.22-7.62 (m, 9H), 7.93 (t, J=7.5 Hz, 1H), 8.10-8.21 (m, 2H), 8.34 (d, J=7.5 Hz, 1H), 8.63 (d, J=9.0 Hz, 1H), 9.11 (d, J=8.1 Hz, 1H), 10.60 (d, J=5.4 Hz, 1H) ppm; $^{13}$C NMR (75 MHz, CDCl$_3$) δ 17.1, 29.1, 57.0, 82.2, 88.4, 118.4, 121.8, 122.5, 126.9, 127.7, 128.9, 130.0, 130.2, 131.2, 131.9, 136.2, 137.8, 140.0, 140.7, 147.5, 150.5 ppm.

Example 42

Synthesis of compound 2-[5-(1,1'-biphenyl-4-yl)-pent-4-ynyl]-isoquinolinium bromide

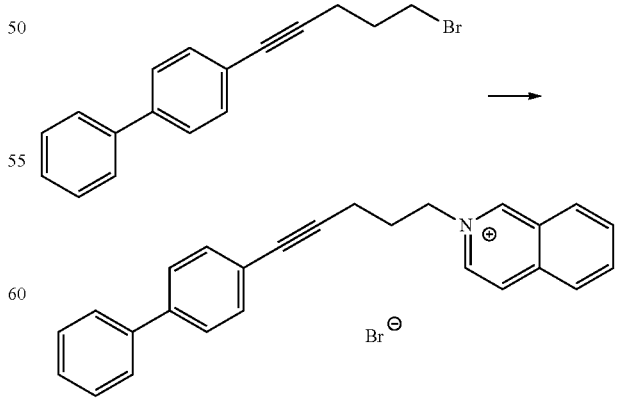

A mixture of 4-(5-bromo-1-pentynl)-1,1'-biphenyl (325 mg, 1.09 mmol) and isoquinoline (1 mL) was heated at 60-70° C. for 12 hrs. The resulted mixture was washed with diethyl ether and then dissolved in water (30 mL). The aqueous solution was extracted with ethyl acetate (30 mL×3). Water was removed by lyophilization to afford 340 mg of the title compound. Yield: 73%. $^1$H NMR (300 MHz, CDCl$_3$) δ 2.51 (m, 2H), 2.72 (t, J=6.3 Hz, 2H), 5.34 (t, J=6.6 Hz, 2H), 7.16 (d, J=8.7 Hz, 1H), 7.30-7.57 (m, 9H), 7.88 (m, 2H), 8.01 (d, J=3.9 Hz, 1H), 8.29 (d, J=6.6 Hz, 1H), 8.69 (d, J=8.4 Hz, 1H), 8.87 (d, J=6.6 Hz, 1H), 11.14 (s, 1H) ppm; $^{13}$C NMR (75 MHz, CDCl$_3$) δ 16.9, 30.2, 60.8, 82.3, 88.0, 121.7, 126.1, 126.8, 126.9, 127.0, 127.7, 127.9, 128.9, 131.26, 131.32, 131.8, 134.6, 137.0, 140.1, 140.5, 150.9 ppm.

Example 43

Synthesis of compound 1-[5-(1,1'-biphenyl-4-yl)-pent-4-ynyl]-3-butyl-pyridinium bromide

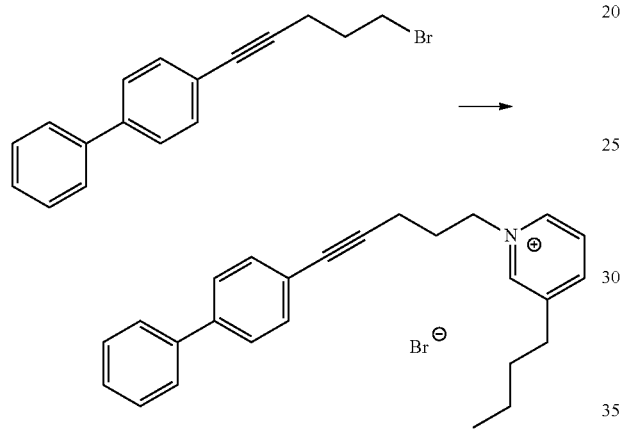

A mixture of 4-(5-bromo-1-pentynl)-1,1'-biphenyl (254 mg, 0.85 mmol) and 3-n-butylpyridine (0.5 mL) was heated at 60-70° C. for 12 hrs. The resulted mixture was washed with diethyl ether and then dissolved in water (20 mL). The aqueous solution was extracted with ethyl acetate (30 mL×3). Water was removed by lyophilization to afford 263 mg of the title compound. Yield: 71%. $^1$H NMR (300 MHz, CDCl$_3$) δ 0.91 (t, J=7.2 Hz, 3H), 1.36 (m, 2H), 1.63 (m, 2H), 2.44 (m, 2H), 2.67 (t, J=6.6 Hz, 2H), 2.84 (t, J=7.8 Hz, 2H), 5.22 (t, J=6.9 Hz, 2H), 7.28-7.63 (m, 9H), 8.04 (dd, J=7.8, 6.0 Hz, 1H), 8.17 (d, J=8.1 Hz, 1H), 9.39 (s, 1H), 9.49 (d, J=5.7 Hz, 1H) ppm; $^{13}$C NMR (75 MHz, CDCl$_3$) δ 14.0, 16.7, 22.4, 30.5, 32.5, 32.6, 60.9, 82.4, 88.0, 121.9, 126.9, 127.7, 128.0, 128.9, 132.0, 140.1, 140.8, 142.9, 144.2, 144.3, 144.9 ppm.

Example 44

Synthesis of compound 1-[5-(1,1'-biphenyl-4-yl)-pent-4-ynyl]-3-phenyl-pyridinium bromide

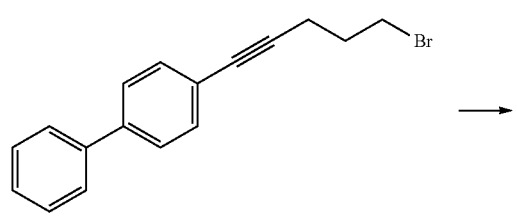

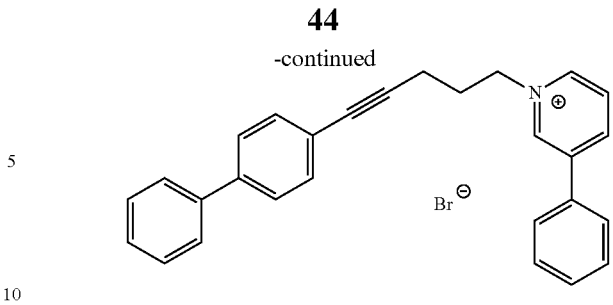

A mixture of 4-(5-bromo-1-pentynl)-1,1'-biphenyl (207 mg, 0.69 mmol) and 3-phenylpyridine (0.4 mL) was heated at 60-70° C. for 12 hrs. The resulted mixture was washed with diethyl ether, and then dissolved in water (30 mL). The aqueous solution was extracted with ethyl acetate (30 mL×5). Water was removed by lyophilization to afford 206 mg of the title compound. Yield: 66%. $^1$H NMR (300 MHz, CD3OD) δ 2.37 (m, 2H), 2.67 (t, J=6.3 Hz, 2H), 4.93 (t, J=6.9 Hz, 2H), 7.18-7.59 (m, 12H), 7.74 (m, 2H), 8.09 (dd, J=8.1, 6.0 Hz, 1H), 8.65 (d, J=8.1 Hz, 1H), 9.05 (d, J=5.7 Hz, 1H), 9.46 (s, 1H) ppm; $^{13}$C NMR (75 MHz, CD3OD) δ 17.5, 30.9, 62.6, 82.9, 89.2, 123.2, 127.7, 128.5, 128.7, 129.4, 130.0, 130.6, 131.4, 133.1, 134.2, 141.0, 141.6, 142.3, 144.0, 144.2 ppm.

Example 45

Synthesis of compound 1-[5-(1,1'-biphenyl-4-yl)-pent-4-ynyl]-1-pyridinium bromide

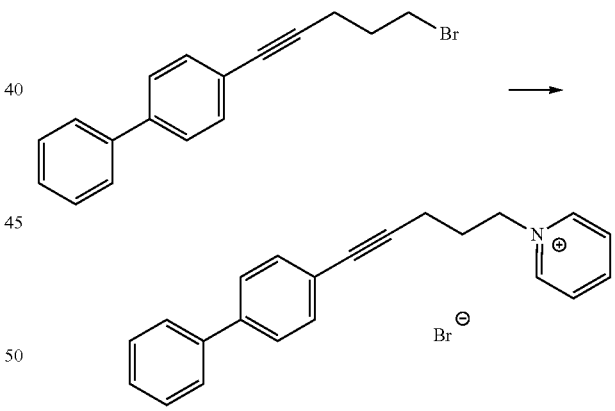

A mixture of 4-(5-bromo-1-pentynl)-1,1'-biphenyl (162 mg, 0.54 mmol) and pyridine (1 mL) was heated at 60-70° C. for 12 hrs. The resulted mixture was washed with diethyl ether and then dissolved in water (10 mL). The aqueous solution was extracted with ethyl acetate (30 mL×3). Water was removed by lyophilization to afford 195 mg of the title compound. Yield: 95%. $^1$H NMR (300 MHz, CDCl$_3$) δ 2.42 (m, 2H), 2.67 (t, J=6.6 Hz, 2H), 5.21 (t, J=6.9 Hz, 2H), 7.23-7.62 (m, 9H), 8.10 (t, J=6.9 Hz, 2H), 8.43 (t, J=7.8 Hz, 2H), 9.64 (d, J=6.0 Hz, 2H) ppm; $^{13}$C NMR (75 MHz, CDCl$_3$) δ 16.7, 30.5, 60.9, 82.3, 87.8, 121.8, 126.8, 127.6, 128.4, 128.8, 132.0, 139.9, 140.6, 145.27, 145.32 ppm.

Example 46

Synthesis of compound [1,1'-biphenyl]-4-pentanol

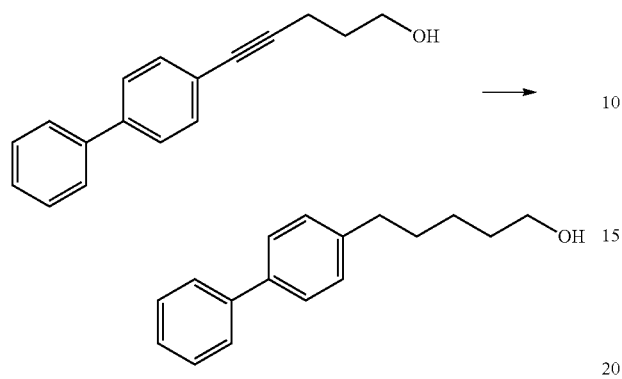

5-(1,1'-biphenyl-4-yl)-4-pentyn-1-ol (3.89 g, 16.46 mmol) was dissolved in methanol (30 mL), and 10% Pd/C (2.5% w/w) was added. The resulting mixture was hydrogenated on a Parr hydrogenation apparatus (45 psi) for 4 hrs. The catalyst was removed by filtration through a Celite pad. The filter cake was rinsed with methanol, and the combined organic liquors were concentrated under reduced pressure. The crude product was purified by column chromatography (hexanes:ethyl acetate 1:1) to afford 3.48 g of the title compound. Yield: 88%. $^1$H NMR (300 MHz, CDCl$_3$) δ 1.35-1.48 (m, 3H), 1.55-1.74 (m, 4H), 2.66 (t, J=7.5 Hz, 2H), 3.64 (t, J=6.6 Hz, 2H), 7.21-7.60 (m, 9H) ppm; $^{13}$C NMR (75 MHz, CDCl$_3$) δ 25.7, 31.5, 32.9, 35.8, 63.1, 127.08, 127.13, 128.8, 128.9, 138.7, 141.2, 141.8 ppm.

Example 47

Synthesis of compound 4-(5-bromopentyl)-1,1'-biphenyl

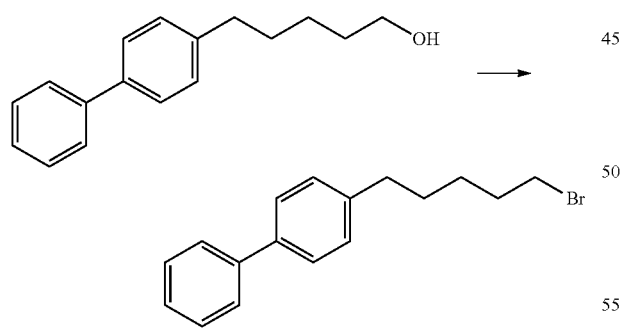

[1,1'-biphenyl]-4-pentanol (3.34 g, 13.90 mmol) and carbon tetrabromide (5.99 g, 18.07 mmol) were dissolved in dry methylene chloride (20 mL) and cooled to 0° C. Triphenyl phosphine (4.98 g, 18.07 mmol) in methylene chloride (10 mL) was added dropwise, and the mixture was stirred for 1 h at 0° C. The mixture was poured into hexanes (100 mL) and then filtered through a short silica gel column, washed with ethylacetate/hexanes (1/4). The combined organic solvents were evaporated to dryness under reduced pressure. The resulting residue was purified by column chromatography (hexanes:ethylacetate 30:1) to afford 4.18 g of the title compound. Yield: 99%. $^1$H NMR (300 MHz, CDCl$_3$) δ 1.52 (m, 2H), 1.67 (m, 2H), 1.91 (m, 2H), 2.67 (t, J=7.5 Hz, 2H), 3.41 (t, J=6.9 Hz, 2H), 7.21-7.60 (m, 9H) ppm; $^{13}$C NMR (75 MHz, CDCl$_3$) δ 28.2, 30.9, 33.0, 34.1, 35.6, 127.1, 127.2, 128.8, 128.9, 138.8, 141.2, 141.5 ppm.

Example 48

Synthesis of compound 1-[5-(1,1'-biphenyl-4-yl)-pentyl]-2-methyl-pyridinium bromide

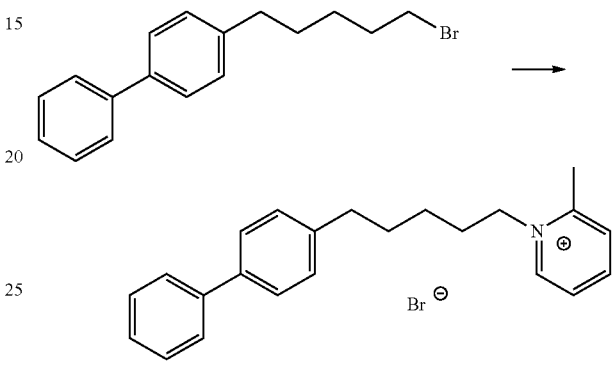

A mixture of 4-(5-bromopentyl)-1,1'-biphenyl (358 mg, 1.18 mmol) and 2-picoline (1 mL) was heated at 60-70° C. for 12 hrs. The resulting mixture was washed with diethyl ether and then dissolved in water (15 mL). The aqueous solution was extracted with diethyl ether (30 mL×3). Water was removed by lyophilization to afford 393 mg of the title compound. Yield: 84%. $^1$H NMR (300 MHz, CDCl$_3$) δ 1.53 (m, 2H), 1.71 (m, 2H), 1.95 (m, 2H), 2.65 (t, J=7.5 Hz, 2H), 2.92 (s, 3H), 4.83 (t, J=8.1 Hz, 2H), 7.20-7.60 (m, 9H), 7.89-8.02 (m, 2H), 8.38 (d, J=7.5 Hz, 1H), 9.53 (d, J=6.0 Hz, 1H) ppm; $^{13}$C NMR (75 MHz, CDCl$_3$) δ 20.9, 25.9, 30.6, 30.8, 35.2, 58.3, 126.3, 126.8, 126.9, 127.0, 128.7, 128.8, 130.3, 138.5, 140.7, 140.9, 145.2, 146.3, 154.1 ppm.

Example 49

Synthesis of compound 1-[5-(1,1'-biphenyl-4-yl)-pentyl]-3-methyl-pyridinium bromide

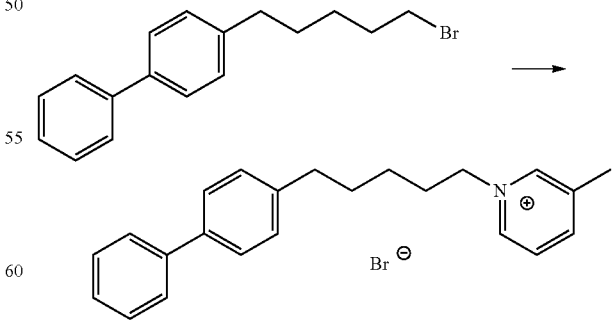

A mixture of 4-(5-bromopentyl)-1,1'-biphenyl (358 mg, 1.18 mmol) and 3-picoline (1 mL) was heated at 60-70° C. for 12 hrs. The resulted mixture was washed with diethyl ether and then dissolved in water (15 mL). The aqueous solution was extracted with diethyl ether (30 mL×3). Water was removed by lyophilization to afford 421 mg of the title compound. Yield: 90%. $^1$H NMR (300 MHz, CDCl$_3$) δ 1.45 (m, 2H), 1.70 (m, 2H), 2.08 (m, 2H), 2.59 (s, 3H), 2.63 (t, J=7.5 Hz, 2H), 4.92 (t, J=7.5 Hz, 2H), 7.18-7.58 (m, 9H), 7.94 (t, J=7.2 Hz, 1H), 8.17 (d, J=8.1 Hz, 1H), 9.26 (d, J=6.3 Hz, 1H), 9.46 (s, 1H) ppm; $^{13}$C NMR (75 MHz, CDCl$_3$) δ 18.8, 25.7, 30.7, 31.9, 35.2, 61.5, 126.8, 126.9, 127.0, 127.7, 128.3, 128.7, 128.8, 138.5, 139.5, 140.7, 141.1, 142.1, 144.5, 145.5 ppm.

Example 50

Synthesis of compound 1-[5-(1,1'-biphenyl-4-yl)-pentyl]-4-methyl-pyridinium bromide

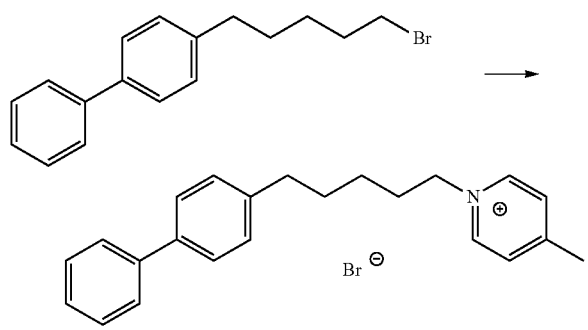

A mixture of 4-(5-bromopentyl)-1,1'-biphenyl (348 mg, 1.15 mmol) and 4-picoline (1 mL) was heated at 60-70° C. for 12 hrs. The resulted mixture was washed with diethyl ether and then dissolved in water (15 mL). The aqueous solution was extracted with diethyl ether (30 mL×3). Water was removed by lyophilization to afford 391 mg of the title compound. Yield: 86%. $^1$H NMR (300 MHz, CDCl$_3$) δ 1.42 (m, 2H), 1.69 (m, 2H), 2.04 (m, 2H), 2.57 (s, 3H), 2.62 (t, J=7.2 Hz, 2H), 4.85 (t, J=7.2 Hz, 2H), 7.15-7.62 (m, 9H), 7.82 (d, J=6.0 Hz, 2H), 9.25 (d, J=6.0 Hz, 2H) ppm; $^{13}$C NMR (75 MHz, CDCl$_3$) δ 22.3, 25.5, 30.7, 31.6, 35.2, 61.0, 126.8, 126.9, 127.1, 128.7, 128.8, 128.9, 138.5, 140.7, 141.1, 144.0, 158.7 ppm.

Example 51

Synthesis of compound 1-[5-(1,1'-biphenyl-4-yl)-pentyl]-2,4-dimethyl-pyridinium bromide

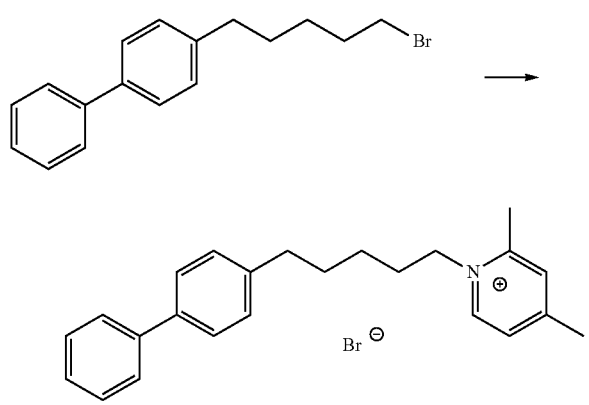

A mixture of 4-(5-bromopentyl)-1,1'-biphenyl (331 mg, 1.09 mmol) and 2,4-lutidine (1 mL) was heated at 60-70° C. for 12 hrs. The resulted mixture was washed with diethyl ether and then dissolved in water (15 mL). The aqueous solution was extracted with diethyl ether (30 mL×3). Water was removed by lyophilization to afford 342 mg of the title compound. Yield: 77%. $^1$H NMR (300 MHz, CDCl$_3$) δ 1.51 (m, 2H), 1.71 (m, 2H), 1.92 (m, 2H), 2.55 (s, 3H), 2.65 (t, J=7.8 Hz, 2H), 2.84 (s, 3H), 4.73 (t, J=7.8 Hz, 2H), 7.20-7.75 (m, 11H), 9.31 (d, J=6.3 Hz, 1H) ppm; $^{13}$C NMR (75 MHz, CDCl$_3$) δ 20.1, 22.0, 25.8, 30.5, 30.8, 35.2, 57.4, 126.7, 126.9, 127.0, 128.2, 128.6, 128.8, 130.4, 138.5, 140.7, 140.9, 145.4, 152.8, 158.4 ppm.

Example 52

Synthesis of compound 1-[5-(1,1'-biphenyl-4-yl)-pentyl]-3,4-dimethyl-pyridinium bromide

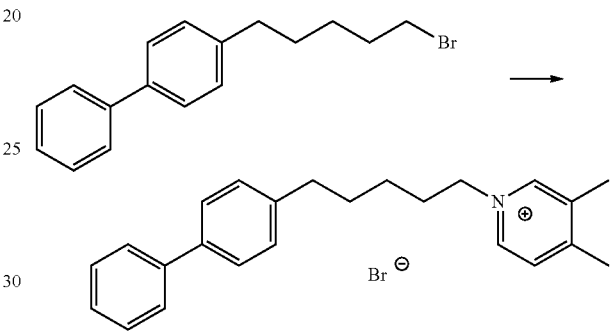

A mixture of 4-(5-bromopentyl)-1,1'-biphenyl (322 mg, 1.06 mmol) and 3,4-lutidine (1 mL) was heated at 60-70° C. for 12 hrs. The resulted mixture was washed with diethyl ether and then dissolved in water (15 mL). The aqueous solution was extracted with diethyl ether (30 mL×3). Water was removed by lyophilization to afford 380 mg of the title compound. Yield: 87%. $^1$H NMR (300 MHz, CDCl$_3$) δ 1.43 (m, 2H), 1.69 (m, 2H), 2.05 (m, 2H), 2.46 (s, 3H), 2.48 (s, 3H), 2.62 (t, J=7.5 Hz, 2H), 4.82 (t, J=7.2 Hz, 2H), 7.18-7.58 (m, 9H), 7.76 (d, J=6.3 Hz, 1H), 9.07 (d, J=6.3 Hz, 1H), 9.29 (s, 1H) ppm; $^{13}$C NMR (75 MHz, CDCl$_3$) δ 17.1, 20.4, 25.6, 30.7, 31.7, 35.2, 60.7, 126.8, 126.9, 127.0, 128.4, 128.7, 128.8, 138.2, 138.5, 140.7, 141.1, 141.7, 143.3, 157.4 ppm.

Example 53

Synthesis of compound 1-[5-(1,1'-biphenyl-4-yl)-pentyl]-3,5-dimethyl-pyridinium bromide

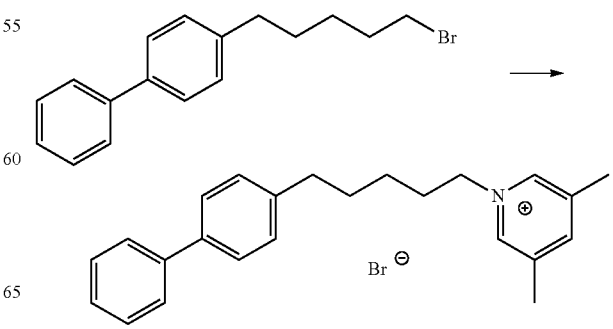

A mixture of 4-(5-bromopentyl)-1,1'-biphenyl (352 mg, 1.16 mmol) and 3,5-lutidine (1 mL) was heated at 60-70° C. for 12 hrs. The resulting mixture was washed with diethyl ether and then dissolved in water (15 mL). The aqueous solution was extracted with diethyl ether (30 mL×3). Water was removed by lyophilization to afford 406 mg of the title compound. Yield: 85%. $^1$H NMR (300 MHz, CDCl$_3$) δ 1.45 (m, 2H), 1.70 (m, 2H), 2.08 (m, 2H), 2.53 (s, 6H), 2.63 (t, J=7.8 Hz, 2H), 4.84 (t, J=7.5 Hz, 2H), 7.18-7.58 (m, 9H), 7.93 (s, 1H), 9.21 (s, 1H) ppm; $^{13}$C NMR (75 MHz, CDCl$_3$) δ 18.6, 25.8, 30.8, 31.9, 35.2, 61.3, 126.8, 126.9, 127.0, 128.7, 128.8, 138.4, 138.7, 140.7, 141.1, 141.7, 146.0 ppm.

Example 54

Synthesis of compound 1-[5-(1,1'-biphenyl-4-yl)-pentyl]-quinolinium bromide

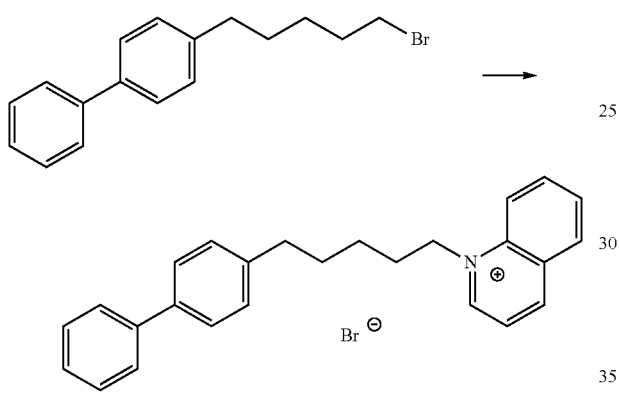

A mixture of 4-(5-bromopentyl)-1,1'-biphenyl (328 mg, 1.08 mmol) and quinoline (1 mL) was heated at 60-70° C. for 12 hrs. The resulting mixture was washed with diethyl ether and then dissolved in water (30 mL). The aqueous solution was extracted with ethyl acetate (30 mL×5). Water was removed by lyophilization to afford 297 mg of the title compound. Yield: 64%. $^1$H NMR (300 MHz, CDCl$_3$) δ 1.58 (m, 2H), 1.70 (m, 2H), 2.13 (m, 2H), 2.62 (t, J=7.5 Hz, 2H), 5.37 (t, J=7.8 Hz, 2H), 7.14-7.58 (m, 9H), 7.92 (d, J=7.5 Hz, 1H), 8.17 (m, 2H), 8.36 (m, 2H), 9.13 (d, J=8.4 Hz, 1H), 10.33 (d, J=5.4 Hz, 1H) ppm; $^{13}$C NMR (75 MHz, CDCl$_3$) δ 26.1, 30.3, 30.9, 35.2, 58.1, 118.3, 122.5, 126.8, 126.9, 127.1, 128.7, 128.8, 129.9, 130.1, 131.1, 136.0, 137.5, 138.5, 140.7, 141.0, 147.3, 150.1 ppm.

Example 55

Synthesis of compound 2-[5-(1,1'-biphenyl-4-yl)-pentyl]-isoquinolinium bromide

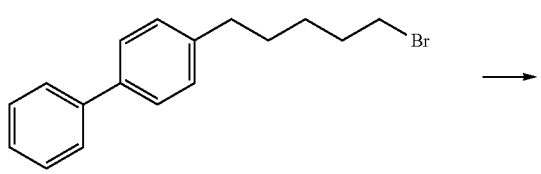

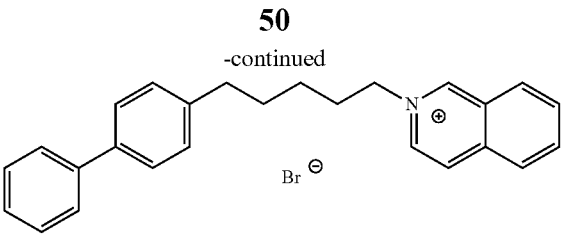

A mixture of 4-(5-bromopentyl)-1,1'-biphenyl (322 mg, 1.06 mmol) and isoquinoline (1 mL) was heated at 60-70° C. for 12 hrs. The resulted mixture was washed with diethyl ether and then dissolved in water (30 mL). The aqueous solution was extracted with ethyl acetate (30 mL×5). Water was removed by lyophilization to afford 278 mg of the title compound. Yield: 61%. $^1$H NMR (300 MHz, CDCl$_3$) δ 1.47 (m, 2H), 1.70 (m, 2H), 2.17 (m, 2H), 2.61 (t, J=7.5 Hz, 2H), 5.07 (t, J=7.5 Hz, 2H), 7.14-7.55 (m, 9H), 7.86 (m, 1H), 8.05 (m, 2H), 8.33 (d, J=6.9 Hz, 1H), 8.70 (d, J=8.1 Hz, 1H), 8.79 (dd, J=6.9, 0.6 Hz, 1H), 10.93 (s, 1H) ppm; $^{13}$C NMR (75 MHz, CDCl$_3$) δ 25.7, 30.7, 31.7, 35.2, 61.5, 126.3, 126.8, 126.9, 127.0, 127.7, 128.7, 128.8, 131.15, 131.22, 134.4, 136.9, 137.2, 138.5, 140.8, 141.0, 150.1 ppm.

Example 56

Synthesis of compound 1-[5-(1,1'-biphenyl-4-yl)-pentyl]-3-butyl-pyridinium bromide

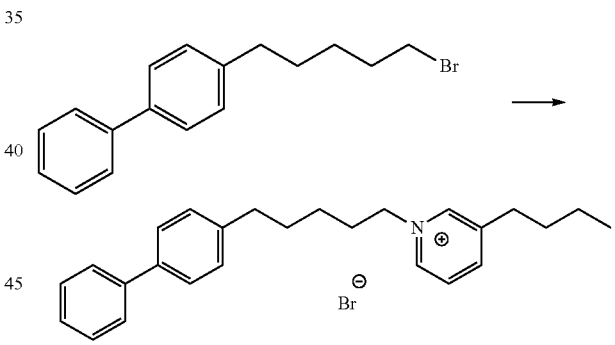

A mixture of 4-(5-bromopentyl)-1,1'-biphenyl (360 mg, 1.19 mmol) and 4-n-butylpyridine (0.5 mL) was heated at 60-70° C. for 12 hrs. The resulting mixture was washed with diethyl ether and then dissolved in water (15 mL). The aqueous solution was extracted with ethyl acetate (30 mL×3). Water was removed by lyophilization to afford 377 mg of the title compound. Yield: 72%. $^1$H NMR (300 MHz, CDCl$_3$) δ 0.92 (t, J=7.2 Hz, 3H), 1.29-1.53 (m, 4H), 1.60-1.80 (m, 4H), 2.08 (m, 2H), 2.63 (t, J=7.5 Hz, 2H), 2.85 (t, J=7.8 Hz, 2H), 4.94 (t, J=7.5 Hz, 2H), 7.18-7.60 (m, 9H), 8.00 (t, J=7.2 Hz, 1H), 8.16 (d, J=8.1 Hz, 1H), 9.29 (d, J=6.0 Hz, 1H), 9.30 (s, 1H) ppm; $^{13}$C NMR (75 MHz, CDCl$_3$) δ 13.9, 22.3, 25.7, 30.8, 32.0, 32.5, 32.6, 35.2, 61.7, 126.8, 127.0, 127.1, 128.0, 128.8, 128.9, 138.6, 140.8, 141.1, 142.5, 144.0, 144.1, 144.6 ppm.

Example 57

Synthesis of compound 1-[5-(1,1'-biphenyl-4-yl)-pentyl]-pyridinium bromide

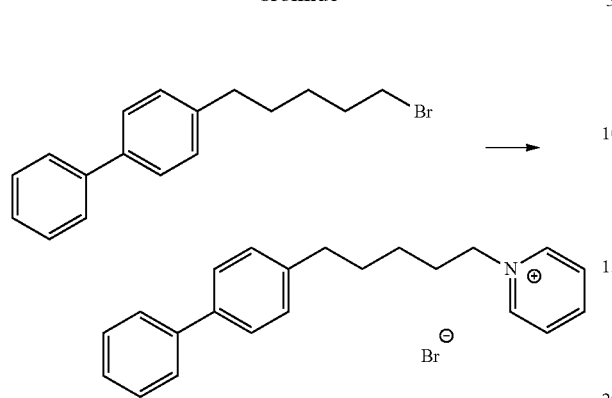

A mixture of 4-(5-bromopentyl)-1,1'-biphenyl (335 mg, 1.10 mmol) and pyridine (1 mL) was heated at 60-70° C. for 12 hrs. The resulted mixture was washed with diethyl ether and then dissolved in water (15 mL). The aqueous solution was extracted with diethyl ether (30 mL×3). Water was removed by lyophilization to afford 381 mg of the title compound. Yield: 90%. $^1$H NMR (300 MHz, CDCl$_3$) δ 1.44 (m, 2H), 1.69 (m, 2H), 2.07 (m, 2H), 2.62 (t, J=7.5 Hz, 2H), 4.96 (t, J=7.5 Hz, 2H), 7.15-7.60 (m, 9H), 8.06 (t, J=6.9 Hz, 2H), 8.42 (d, J=7.8 Hz, 1H), 9.48 (d, J=6.0 Hz, 2H) ppm; $^{13}$C NMR (75 MHz, CDCl$_3$) δ 25.6, 30.7, 31.9, 35.2, 61.8, 126.8, 127.0, 127.1, 128.4, 128.8, 128.9, 138.6, 140.8, 141.0, 145.0 ppm.

Example 58

Synthesis and Structures of Mono-Quaternary Ammonium Compounds Containing Phenylene-Acetylenic Moieties in the N-Alkyl Substituent

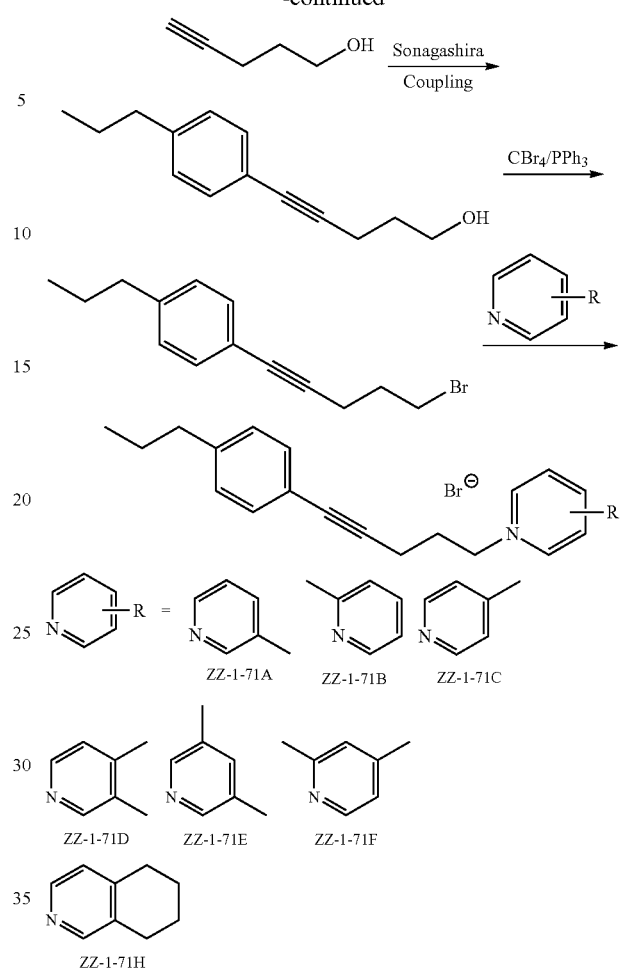

Example 59

Synthesis and Structures of Mono-Quaternary Ammonium Compounds Containing Biphenylene-Acetylenic or Biphenylene-Alkylenic Moieties in the N-Alkyl Substituent

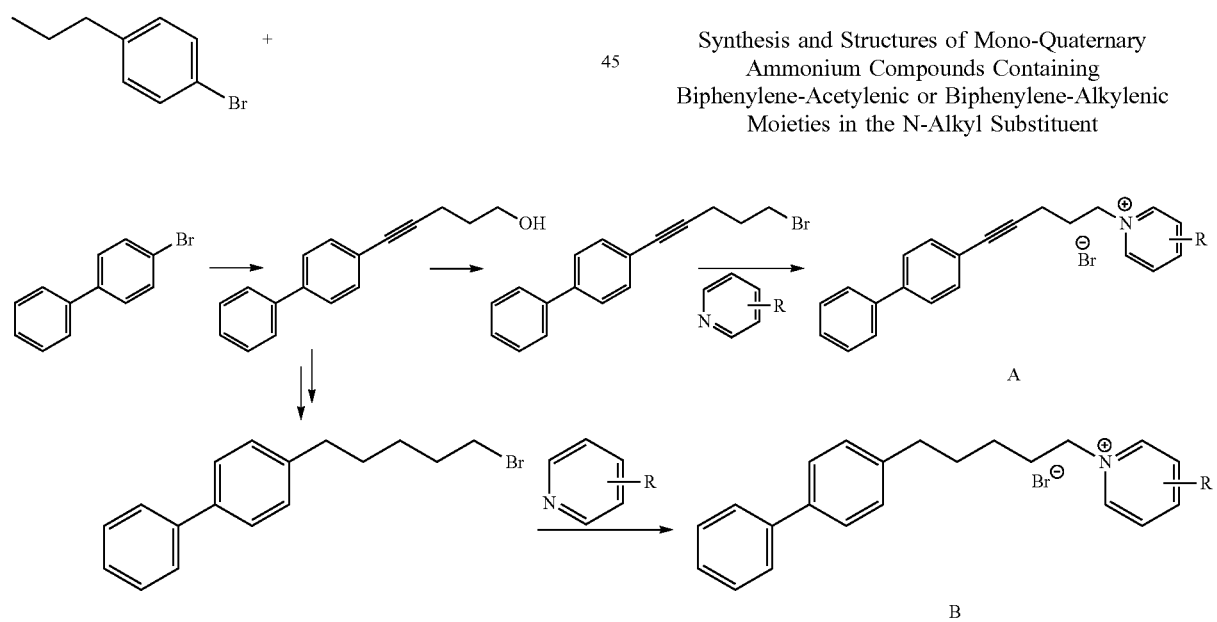

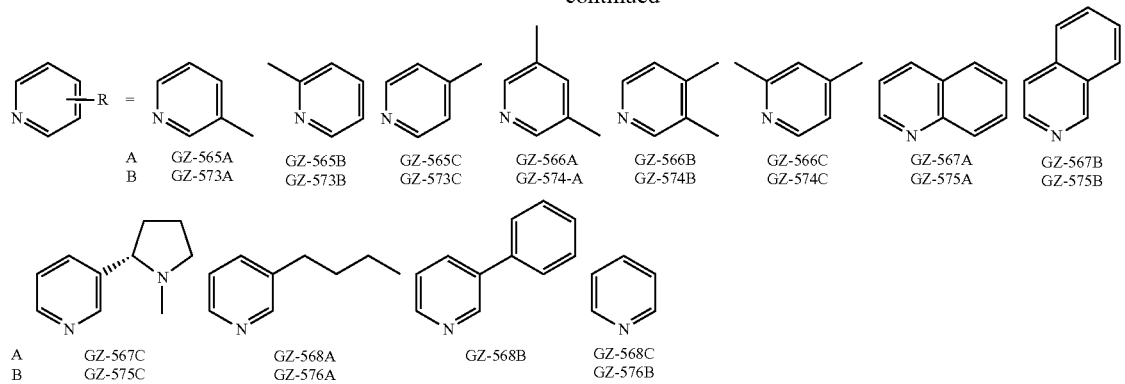

Example 60

Synthesis and Structures of Mono-Quaternary Ammonium Compounds Containing a Terminal 3-Pyridinyl Moiety

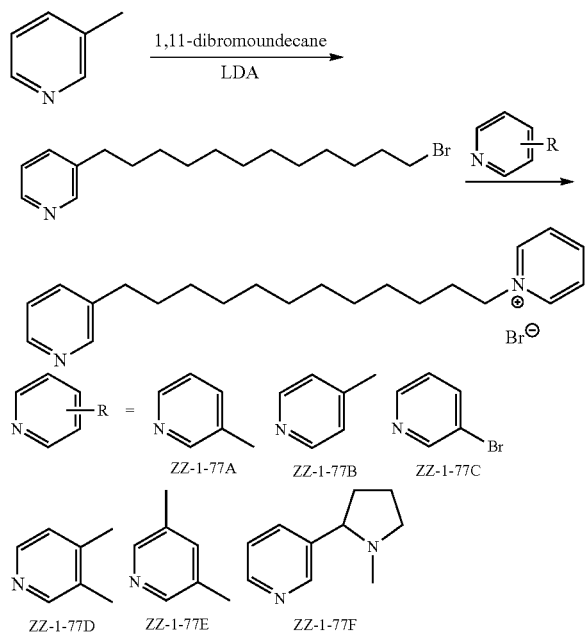

Example 61

Synthesis and Structures of Oxa Analogs of Mono-Quaternary Ammonium Compounds

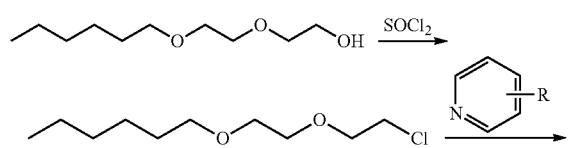

Example 62

Method for the In Vitro Inhibition of [³H]Nicotine Binding and [³H]Methyllycaconitine (MLA) Binding Test compounds of Formula (I), representing the mono quaternary nicotine analogs of the present invention, were evaluated to determine the effect of a test compound on nicotine-binding and methyllycaconitine-binding mediated by nicotine acetylcholine receptors. Table 1 of provides the results of these binding assays.

Whole brain, excluding cortex and cerebellum, was homogenized in 20 volumes of ice-cold buffer containing: 2 mM HEPES, 11.8 mM NaCl, 0.48 mM KCl, 0.25 mM CaCl$_2$, and 0.12 mM MgSO$_4$, pH 7.5. Homogenate was centrifuged (25,000 g, 15 min, 4° C.). Pellets were resuspended in 20 volumes of buffer and incubated at 37° C., for 10 min, cooled to 4° C. and centrifuged (25,000 g, 15 min, 4° C.). Pellets were resuspended and centrifuged using the same conditions. Final pellets were stored in assay buffer, containing: 20 mM HEPES, 118 mM NaCl, 4.8 mM KCl, 2.5 mM CaCl$_2$, and 1.2 mM MgSO$_4$, pH 7.5 at −70° C. Upon use, final pellets were resuspended in ~20 volumes of assay buffer. Samples (250 µl) contained 100-140 µg of membrane protein, 3 nM [³H]nicotine or 3 nM [³H]methyllycaconitine (MLA), and test compounds of Formula (I) (100 nM) in assay buffer containing 50 mM Tris. A control sample absent test compounds of Formula (I) was also prepared. In the [³H]nicotine-binding assay and [³H]MLA-binding assay, nonspecific-binding was determined in the presence of 10 µM nicotine and 10 µM MLA, respectively. Incubations proceeded for 60 min at a room temperature using 96-well plates, and were terminated by harvesting on Unifilter-96 GF/B filter plates presoaked in 0.5% polyethylenimine, using a Packard FilterMate harvester. After washing 5 times with 350 µl ice-cold assay buffer, the filter plates were dried (60 min, 4° C.), bottom-sealed, and filled with Packard's MicroScint 20 cocktail (40 µl/well). After 60 min, filter plates were top-sealed, and levels of radioactivity were determined using a Packard TopCount. Protein concentrations were determined using the Bradford dye-binding procedure using bovine serum albumin as a standard protein.

Example 63

Method for the Analysis of Rat Striatal Slices for Inhibition of Nicotine-Evoked [³H]Neurotransmitter Release Rat striatal slices (500 µm thickness, 6-8 mg wet weight) were incubated for 30 minutes in Krebs buffer (118 mM NaCl, 4.7 mM KCl, 1.2 mM $MgCl_2$, 1.0 mM $NaH_2PO_4$, 1.3 mM $CaCl_2$, 11.1 mM glucose, 25 mM $NaHCO_3$, 0.11 mM L-ascorbic acid, and 0.004 mM disodium EDTA at pH 7.4, and saturated with 95% $O_2$/5% $CO_2$) in a metabolic shaker at 34° C. Slices were rinsed with 15 mL of fresh buffer, and were incubated for an additional 30 minutes in fresh buffer containing 0.1 µM [³H]dopamine (DA; 6 slices/3 mL). Subsequently, slices were rinsed with 15 mL of fresh buffer and transferred to a glass superfusion chamber. Slices were superfused (1.0 mL/min) for 60 minutes with Krebs buffer containing nomifensine (10 µM) and pargyline (10 µM), and maintained at 34° C., pH 7.4, with continual aeration (95% $O_2$/5% $CO_2$). Two five minute samples (5 mL each) were collected to determine basal outflow of [³H]DA. The test compounds of Formula (I) were added to the superfusion buffer after the collection of the second sample, and were maintained in the buffer until 12 consecutive five minute samples were collected. Subsequently, S-(−)-nicotine (10 µM) was added to the buffer, and an additional 12 consecutive five minute samples were collected. At the end of the experiment, each slice was solubilized, and the [³H] content of the tissue determined.

Radioactivity in the superfusate and tissue samples was determined by liquid scintillation spectroscopy. Fractional release of tritium collected in each sample was divided by the total tritium present in the tissue at the time of sample collection, and the fractional release of tritium collected was expressed as a percentage of total tritium. Basal [³H]outflow was calculated from the average of the tritium collected in the two five minute samples just before addition of a test compound of Formula (I). The sum of the increase in collected tritium resulting from either exposure to a test compound of Formula (I), or exposure to S(−) nicotine in the absence and presence of a test compound of Formula (I) equaled total [³H]overflow. [³H]Overflow was calculated by subtracting the [³H]outflow during an equivalent period of pre-stimulation from the values in samples collected during and after drug exposure. Inasmuch as the radio-labeled compounds were not separated and identified, the tritium collected in superfusate is referred to as either [³H]outflow or [³H]overflow, rather than as [³H]DA. [³H]Overflow primarily represents [³H]DA in the presence of nomifensine and pargyline in the superfusion buffer.

The mono quaternary analogs of Formula (I) were evaluated for their ability to evoke [³H]DA release from rat striatal slices. In addition, the classical competitive nicotinic antagonist DHβE was also examined in this assay for comparison. None of the compounds examined had any significant [³H]DA releasing properties in this assay in the concentration range tested.

The quaternary analogs of Formula (I) were also evaluated for their ability to inhibit NIC-evoked [³H]DA release. In these experiments, the striatal slices were superfused for 60 minutes with 100 nM concentration of the quaternary analogs prior to NIC (10 µM) exposure. Antagonist activity was evaluated by comparing the NIC-evoked [³H]overflow in the absence and presence of the analogs. The relative order of potency of the quaternary analogs of Formula (I) for inhibition of NIC-evoked [³H]DA release from rat striatal slices is illustrated in Table 1.

TABLE 1

Inhibition of [³H]NIC and [³H]MLA Binding to Rat Striatal Nicotinic Receptors and Inhibition of Nicotine-evoked [³H]Dopamine Release from Superfused Rat Striatal Slices by Mono Quaternary Ammonium Salts of Formula (I).

| TEST COMPOUND OF FORMULA (I) | Inhibition of [³H]Nicotine binding | Inhibition of [³H]MLA binding | Inhibition of Nicotine-evoked [³H]DA release |
|---|---|---|---|
| ZZ-1-49 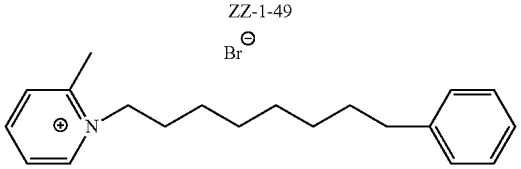 | 0%$^a$ | 0%$^a$ | 62%$^a$ |
| ZZ-1-104 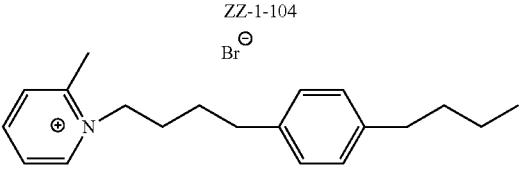 | 0% | 0% | ND |

TABLE 1-continued

Inhibition of [³H]NIC and [³H]MLA Binding to Rat Striatal Nicotinic Receptors and Inhibition of Nicotine-evoked
[³H]Dopamine Release from Superfused Rat Striatal Slices by Mono Quaternary Ammonium Salts of Formula (I).

| TEST COMPOUND OF FORMULA (I) | Inhibition of [³H]Nicotine binding | Inhibition of [³H]MLA binding | Inhibition of Nicotine-evoked [³H]DA release |
|---|---|---|---|
| ZZ-1-70 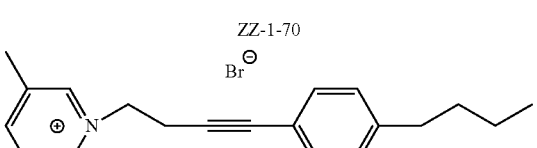 | 0% | 0% | 11% |
| ZZ-1-94 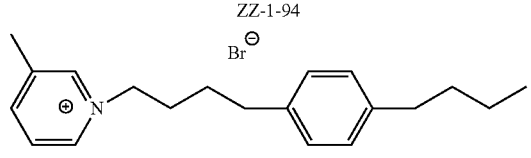 | 4% | 2% | 33% |
| ZZ-1-137A 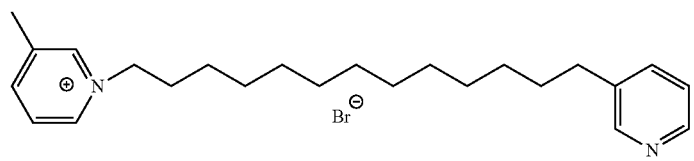 | 0% | 2% | 31% |
| ZZ-1-47 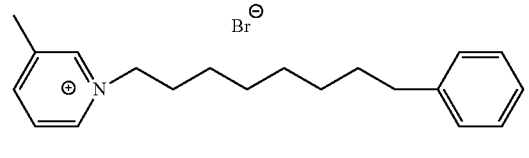 | $K_i$ > 100 | Ki > 100 | 0% |
| ZZ-1-48 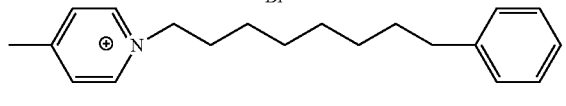 | Ki > 100 | Ki; 27 ± 11 | 12% |
| ZZ-1-71 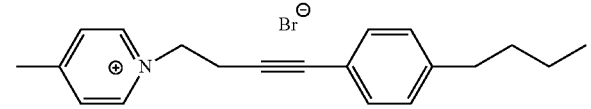 | 6% | 3% | 11% |
| ZZ-1-95 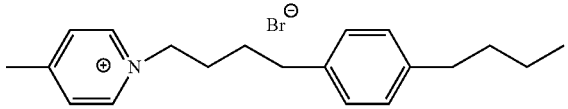 | 5% | 0% | 58% |
| ZZ-1-76 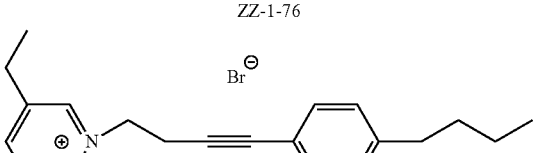 | 0% | 0% | ND |

TABLE 1-continued

Inhibition of [³H]NIC and [³H]MLA Binding to Rat Striatal Nicotinic Receptors and Inhibition of Nicotine-evoked [³H]Dopamine Release from Superfused Rat Striatal Slices by Mono Quaternary Ammonium Salts of Formula (I).

| TEST COMPOUND OF FORMULA (I) | Inhibition of [³H]Nicotine binding | Inhibition of [³H]MLA binding | Inhibition of Nicotine-evoked [³H]DA release |
|---|---|---|---|
| ZZ-1-74 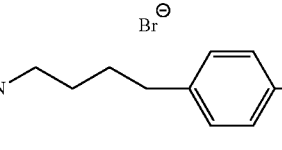 | Ki > 100 | Ki; 3.7 ± 0.3 | 70 |
| ZZ-1-98 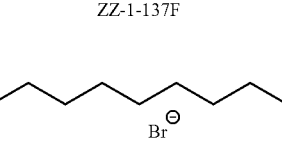 | Ki > 100 | Ki; 14 ± 3.7 | ND |
| ZZ-1-137F 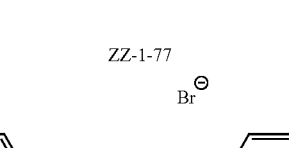 | Ki > 100 | Ki; 7.2 ± 1.0 | 0% |
| ZZ-1-77 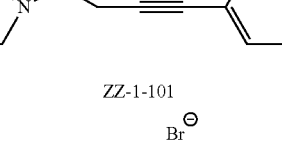 | 0% | 0% | ND |
| ZZ-1-101 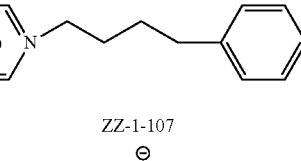 | 0% | 0% | 64 |
| ZZ-1-107 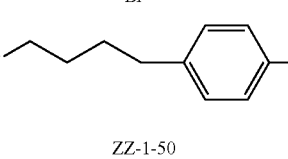 | 6% | 0% | 19% |
| ZZ-1-50 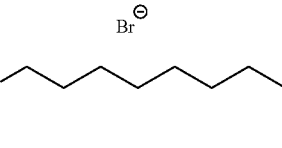 | 0% | 9% | 14% |
| ZZ-1-73 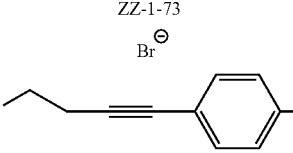 | 0% | 10% | ND |

TABLE 1-continued

Inhibition of [³H]NIC and [³H]MLA Binding to Rat Striatal Nicotinic Receptors and Inhibition of Nicotine-evoked [³H]Dopamine Release from Superfused Rat Striatal Slices by Mono Quaternary Ammonium Salts of Formula (I).

| TEST COMPOUND OF FORMULA (I) | Inhibition of [³H]Nicotine binding | Inhibition of [³H]MLA binding | Inhibition of Nicotine-evoked [³H]DA release |
|---|---|---|---|
| ZZ-1-137D | 3% | 0% | 20% |
| ZZ-1-97 | 0% | 0% | ND |
| ZZ-1-72 | 0% | 0% | ND |
| ZZ-1-96 | 0% | 0% | ND |
| ZZ-1-137C | 0% | 0% | 35% |
| GZ-565B | 2% | 7% | 45% |
| GZ-573B | ND | ND | 45% |

TABLE 1-continued

Inhibition of [³H]NIC and [³H]MLA Binding to Rat Striatal Nicotinic Receptors and Inhibition of Nicotine-evoked
[³H]Dopamine Release from Superfused Rat Striatal Slices by Mono Quaternary Ammonium Salts of Formula (I).

| TEST COMPOUND OF FORMULA (I) | Inhibition of [³H]Nicotine binding | Inhibition of [³H]MLA binding | Inhibition of Nicotine-evoked [³H]DA release |
|---|---|---|---|
| GZ-565A 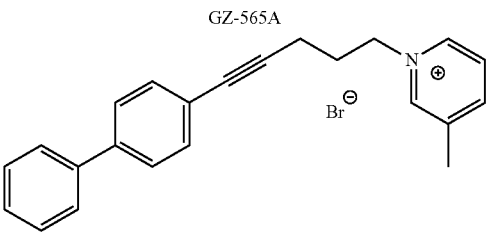 [SMILES: Cc1ccc[n+](CCCC#Cc2ccc(-c3ccccc3)cc2)c1 ; [Br-]] | 0 | 2% | 41% |
| GZ-573A 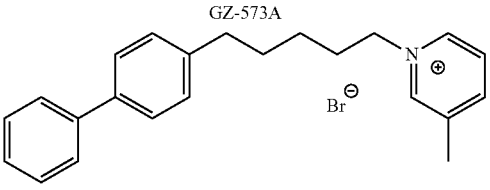 [SMILES: Cc1ccc[n+](CCCCCc2ccc(-c3ccccc3)cc2)c1 ; [Br-]] | 4% | 7% | 55% |
| GZ-573C 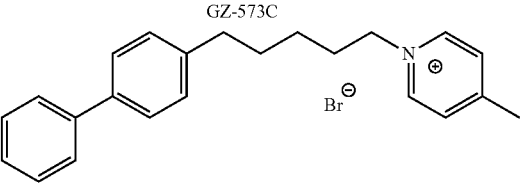 [SMILES: Cc1cc[n+](CCCCCc2ccc(-c3ccccc3)cc2)cc1 ; [Br-]] | ND | ND | 18% |
| GZ-565C 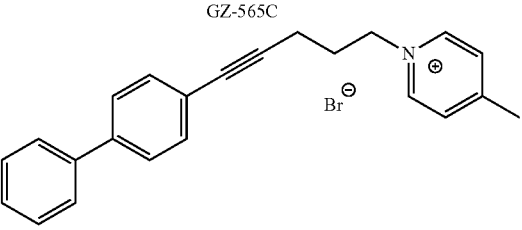 [SMILES: Cc1cc[n+](CCCC#Cc2ccc(-c3ccccc3)cc2)cc1 ; [Br-]] | 0% | 3% | 40% |
| GZ-566A 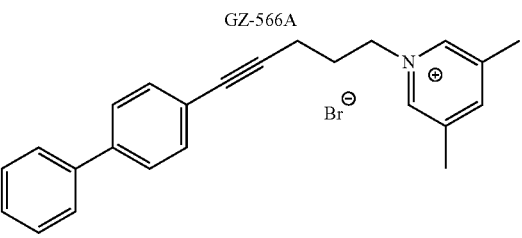 [SMILES: Cc1cc(C)c[n+](CCCC#Cc2ccc(-c3ccccc3)cc2)c1 ; [Br-]] | 8% | 3% | 51% |
| GZ-574A 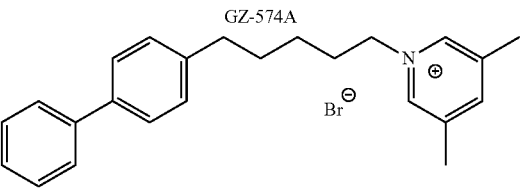 [SMILES: Cc1cc(C)c[n+](CCCCCc2ccc(-c3ccccc3)cc2)c1 ; [Br-]] | ND | ND | 51% |

TABLE 1-continued

Inhibition of [³H]NIC and [³H]MLA Binding to Rat Striatal Nicotinic Receptors and Inhibition of Nicotine-evoked [³H]Dopamine Release from Superfused Rat Striatal Slices by Mono Quaternary Ammonium Salts of Formula (I).

| TEST COMPOUND OF FORMULA (I) | Inhibition of [³H]Nicotine binding | Inhibition of [³H]MLA binding | Inhibition of Nicotine-evoked [³H]DA release |
|---|---|---|---|
| GZ-566B | 0% | 8% | 20% |
| GZ-574B | ND | ND | 38% |
| GZ-566C | 2% | 6% | 5% |
| GZ-574C | ND | ND | 39% |
| GZ-567A | 1% | 7% | 23% |
| GZ-575A | ND | ND | 61% |

TABLE 1-continued

Inhibition of [³H]NIC and [³H]MLA Binding to Rat Striatal Nicotinic Receptors and Inhibition of Nicotine-evoked
[³H]Dopamine Release from Superfused Rat Striatal Slices by Mono Quaternary Ammonium Salts of Formula (I).

| TEST COMPOUND OF FORMULA (I) | Inhibition of [³H]Nicotine binding | Inhibition of [³H]MLA binding | Inhibition of Nicotine-evoked [³H]DA release |
|---|---|---|---|
| GZ-567B 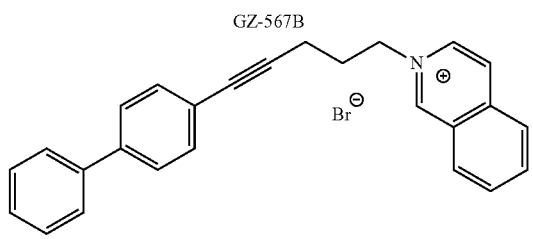 [SMILES: C(#Cc1ccc(-c2ccccc2)cc1)CCC[n+]1ccc2ccccc2c1 ; [Br-]] | 0% | 6% | ND |
| GZ-575B 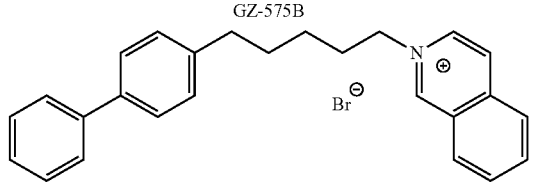 [SMILES: c1ccc(-c2ccc(CCCCC[n+]3ccc4ccccc4c3)cc2)cc1 ; [Br-]] | 0% | 6% | ND |
| GZ-567C 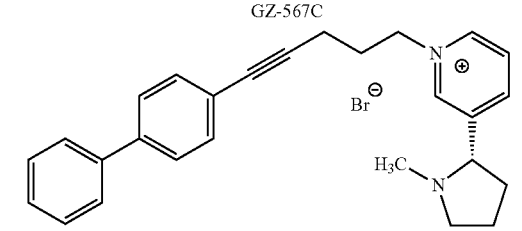 [SMILES: CN1CCC[C@H]1c1ccc[n+](CCCC#Cc2ccc(-c3ccccc3)cc2)c1 ; [Br-]] | 20% | 6% | 47% |
| GZ-575C 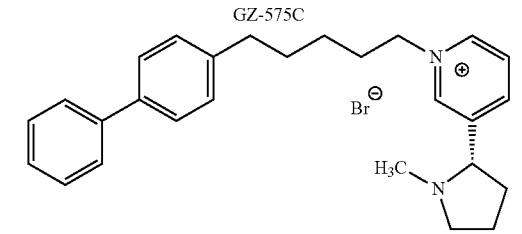 [SMILES: CN1CCC[C@H]1c1ccc[n+](CCCCCc2ccc(-c3ccccc3)cc2)c1 ; [Br-]] | ND | ND | 51% |
| GZ-568A 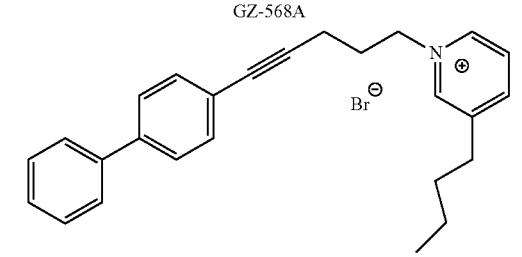 [SMILES: CCCCc1ccc[n+](CCCC#Cc2ccc(-c3ccccc3)cc2)c1 ; [Br-]] | 0% | 9% | 50% |
| GZ-576A 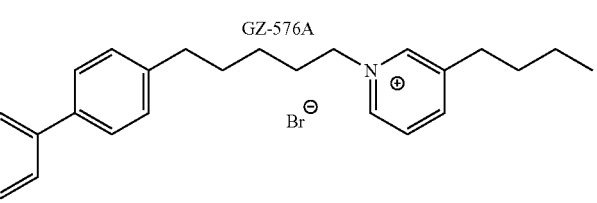 | ND | ND | 43% |

TABLE 1-continued

Inhibition of [³H]NIC and [³H]MLA Binding to Rat Striatal Nicotinic Receptors and Inhibition of Nicotine-evoked [³H]Dopamine Release from Superfused Rat Striatal Slices by Mono Quaternary Ammonium Salts of Formula (I).

| TEST COMPOUND OF FORMULA (I) | Inhibition of [³H]Nicotine binding | Inhibition of [³H]MLA binding | Inhibition of Nicotine-evoked [³H]DA release |
|---|---|---|---|
| GZ-568B | 8% | 6% | ND |
| GZ-568C | 2% | 6% | 34% |
| GZ-576B | ND | ND | 30% |

It will be appreciated that, although specific embodiments of the invention have been described herein for purposes of illustration, various modifications may be made without departing from the spirit and the scope of the invention. All such modifications and variations ore intended to be included herein within the scope of this disclosure and the present invention and protected by the following claims.

We claim:
1. A compound of Formula (I):

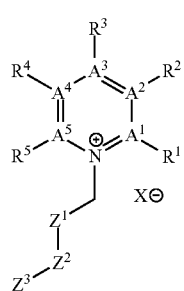

(I)

wherein $A^1$, $A^2$, $A^3$, $A^4$, and $A^5$ are each carbon;
wherein three of $R^1$, $R^3$, $R^4$, and $R^5$ are hydrogen, alkyl, or substituted alkyl, and
$R^1$ and $R^2$ or $R^2$ and $R^3$ together with the carbons to which they are attached independently form a three- to eight-member cycloalkane, cycloalkene, aryl, heterocycle with one to three hetero atoms in the ring, or substituted heterocycle with one to three hetero atoms in the ring;
wherein $Z^1$ is absent or is selected from the group consisting of alkyl, substituted alkyl, cycloalkyl, alkenyl, alkynyl, phenylene, and alkoxy;
wherein $Z^2$ is selected from the group consisting of substituted alkyl, cycloalkyl, alkenyl, alkynyl, arylene, heterocycle, substituted heterocycle, and alkoxy;
wherein $Z^3$ is selected from propyl, butyl, hexyl, substituted alkyl, cycloalkyl, alkenyl, alkynyl, aryl, heterocycle, and substituted heterocycle;
wherein $X^-$ is an inorganic or organic anion,
wherein substituted alkyl is an alkyl substituted with one or more substituents selected from the group consisting of hydroxy, lower-alkyl alkoxy, lower-alkyl mercapto, halogen, trifluoromethyl, cyano, nitro, amino, carboxyl, carbamate, sulfonyl, sulfonamide, an aryl group, and a heterocyclic group, and
wherein substituted heterocycle is a heterocycle substituted with one or more substituents selected from the group consisting of hydroxy, lower-alkyl alkoxy, lower-alkyl mercapto, halogen, trifluoromethyl, cyano, nitro, amino, carboxyl, carbamate, sulfonyl, sulfonamide, an aryl group, and a heterocyclic group.
2. The compound of claim 1, wherein $A^1$, $A^2$, $A^3$, $A^4$, and $A^5$ are carbon;
wherein $R^1$ is hydrogen, methyl, forms a six membered ring with $A^1$, $A^2$ and $R^2$ and with $R^1$ and $R^2$ providing four saturated carbon atoms, or forms a phenyl group with $A^1$, $A^2$ and $R^2$;

wherein $R^2$ is hydrogen, methyl, ethyl, butyl, phenyl, 3-hydroxypropyl, forms a six membered ring with $A^1$, $A^2$ and $R^1$ and with $R^1$ and $R^2$ providing four saturated carbon atoms, forms a phenyl group with $A^1$, $A^2$ and $R^1$, forms a six membered ring with $A^2$, $A^3$ and $R^3$ and with $R^2$ and $R^3$ providing four saturated carbon atoms, or forms a phenyl group with $A^2$, $A^3$ and $R^3$;

wherein $R^3$ is hydrogen, methyl, forms a six membered ring with $A^2$, $A^3$ and $R^2$ and with $R^2$ and $R^3$ providing four saturated carbon atoms, or forms a phenyl group with $A^2$, $A^3$ and $R^2$;

wherein $R^4$ is hydrogen or methyl;

wherein $R^5$ is hydrogen;

wherein $Z^1$ is absent, butyl, but-3-ynyl, pentyl, pent-4-ynyl or 2-ethoxy;

wherein $Z^2$ is para-phenylene, or 2-ethoxy;

wherein $Z^3$ is propyl, butyl, but-1-ynyl, hex-1-ynyl, phenyl, or 3-pyridinyl;

and wherein X is chloride, bromide or iodide.

3. The compound of claim 1, wherein $A^1$, $A^2$, $A^3$, $A^4$, and $A^5$ are carbon;

wherein $R^1$ is hydrogen, methyl, forms a six membered ring with $A^1$, $A^2$ and $R^2$ and with $R^1$ and $R^2$ providing four saturated carbon atoms, or forms a phenyl group with $A^1$, $A^2$ and $R^2$;

wherein $R^2$ is hydrogen, methyl, ethyl, 3-hydroxypropyl, forms a six membered ring with $A^1$, $A^2$ and $R^1$ and with $R^1$ and $R^2$ providing four saturated carbon atoms, forms a phenyl group with $A^1$, $A^2$ and $R^1$, forms a six membered ring with $A^2$, $A^3$ and $R^3$ and with $R^2$ and $R^3$ providing four saturated carbon atoms, or forms a phenyl group with $A^2$, $A^3$ and $R^3$;

wherein $R^3$ is hydrogen, methyl, forms a six membered ring with $A^2$, $A^3$ and $R^2$ and with $R^2$ and $R^3$ providing four saturated carbon atoms, or forms a phenyl group with $A^2$, $A^3$ and $R^2$;

wherein $R^4$ is hydrogen or methyl;

wherein $R^5$ is hydrogen;

wherein $Z^1$ is absent, butyl, but-3-ynyl, pent-4-ynyl or 2-ethoxy;

wherein $Z^2$ is para-phenylene, or 2-ethoxy;

wherein $Z^3$ is propyl, butyl, but-1-ynyl, hex-1-ynyl, phenyl, or 3-pyridinyl; and wherein X is chloride, bromide or iodide.

4. The compound of claim 1, wherein $A^1$, $A^2$, $A^3$, $A^4$, and $A^5$ are carbon;

wherein $R^1$ is hydrogen, methyl, or forms a phenyl group with $A^1$, $A^2$ and $R^2$;

wherein $R^2$ is hydrogen, methyl, butyl, forms a phenyl group with $A^1$, $A^2$ and $R^1$, or forms a phenyl group with $A^2$, $A^3$ and $R^3$;

wherein $R^3$ is hydrogen, methyl, or forms a phenyl group with $A^2$, $A^3$ and $R^2$;

wherein $R^4$ is hydrogen or methyl;

wherein $R^5$ is hydrogen;

wherein $Z^1$ is pentyl or pent-4-ynyl;

wherein $Z^2$ is para-phenylene;

wherein $Z^3$ is phenyl; and wherein X is bromide.

5. The compound of claim 1 selected from the group consisting of:

2-[4-(4-butyl-phenyl)-butyl]-5,6,7,8-tetrahydro-isoquinolinium bromide;

2-[4-(4-butyl-phenyl)-but-3-ynyl]-5,6,7,8-tetrahydro-isoquinolinium bromide;

2-[13-(3-pyridinyl)-tridecyl]-5,6,7,8-tetrahydro-isoquinolinium bromide;

1-[5-(1,1'-biphenyl-4-yl)-pent-4-ynyl]-quinolinium bromide;

2-[5-(1,1'-biphenyl-4-yl)-pent-4-ynyl]-isoquinolinium bromide;

1-[5-(1,1'-biphenyl-4-yl)-pentyl]-quinolinium bromide;

2-[5-(1,1'-biphenyl-4-yl)-pentyl]-isoquinolinium bromide;

2-[4-(4-propyl-phenyl)-pent-4-ynyl]-5,6,7,8-tetrahydro-isoquinolinium bromide;

1-[2-(2-hexoxy-ethoxy)-ethyl]-5,6,7,8-tetrahydro-quinolinium chloride; and

2-[2-(2-hexoxy-ethoxy)-ethyl]-5,6,7,8-tetrahydro-isoquinolinium chloride.

6. A composition comprising a pharmaceutically acceptable carrier and a compound of claim 1.

7. A composition comprising a pharmaceutically acceptable carrier and a compound of claim 2.

8. A composition comprising a pharmaceutically acceptable carrier and a compound of claim 3.

9. A composition comprising a pharmaceutically acceptable carrier and a compound of claim 4.

10. A composition comprising a pharmaceutically acceptable carrier and a compound of claim 5.

* * * * *